(12) United States Patent
Fish et al.

(10) Patent No.: US 7,378,436 B2
(45) Date of Patent: May 27, 2008

(54) COMPOUNDS

(75) Inventors: Paul Vincent Fish, Sandwich (GB); Michael Jonathan Fray, Sandwich (GB); Alan Stobie, Sandwich (GB); Florian Wakenhut, Sandwich (GB); Gavin Alistair Whitlock, Sandwich (GB); Mark David Andrews, Sandwich (GB); Alan Daniel Brown, Sandwich (GB); Mark Ian Lansdell, Sandwich (GB)

(73) Assignee: Pfizer Inc., New York, NY (US)

( * ) Notice: Subject to any disclaimer, the term of this patent is extended or adjusted under 35 U.S.C. 154(b) by 580 days.

(21) Appl. No.: 10/872,160

(22) Filed: Jun. 17, 2004

(65) Prior Publication Data

US 2005/0137229 A1 Jun. 23, 2005

Related U.S. Application Data

(60) Provisional application No. 60/493,126, filed on Aug. 6, 2003.

(30) Foreign Application Priority Data

Jun. 17, 2003 (GB) .................................. 0314048.0

(51) Int. Cl.
*A61K 31/40* (2006.01)
*C07D 295/10* (2006.01)

(52) U.S. Cl. ...................... 514/408; 548/517; 548/518; 548/523; 548/526; 548/557

(58) Field of Classification Search ................. 548/517, 548/518, 523, 526, 557; 514/408
See application file for complete search history.

(56) References Cited

U.S. PATENT DOCUMENTS

| 3,963,745 | A | 6/1976 | Cale, Jr. et al. | ............. | 260/326 |
|---|---|---|---|---|---|
| 4,020,072 | A | 4/1977 | Hoehn | ..................... | 260/293.6 |
| 5,025,013 | A | 6/1991 | Barreau et al. | | |
| 5,130,312 | A | 7/1992 | Van Daele et al. | | |
| 6,544,922 | B1 * | 4/2003 | Marks et al. | ................ | 502/152 |
| 2004/0006089 | A1 | 1/2004 | Thurieau et al. | | |

FOREIGN PATENT DOCUMENTS

| CH | 628885 | 12/1978 |
|---|---|---|
| DE | 138773 | 11/1979 |
| EP | 0379441 | 1/1990 |
| FR | 2295744 | 12/1975 |
| GB | 1574419 | 9/1980 |
| WO | WO 9718813 | 5/1997 |
| WO | WO 9965881 | 12/1999 |
| WO | WO 0144191 | 6/2001 |
| WO | WO 0166114 | 9/2001 |
| WO | WO 0166521 | 9/2001 |
| WO | WO 0224649 | 3/2002 |
| WO | WO 0224694 | 3/2002 |
| WO | WO 03024928 | 3/2003 |
| WO | WO 03037865 | 5/2003 |
| WO | WO 03045949 | 6/2003 |
| WO | WO 2004000808 | 12/2003 |
| WO | WO 2004009549 | 1/2004 |
| WO | WO 2004022536 | 3/2004 |
| WO | WO 2004058705 | 7/2004 |

OTHER PUBLICATIONS

Harper et al. "The chemistry and pharmacology of . . . " CA 62:2980 (1965).*

(Continued)

*Primary Examiner*—Celia Chang
(74) *Attorney, Agent, or Firm*—Gregg C. Benson; John H. Engelmann

(57) ABSTRACT

A compound of Formula (I)

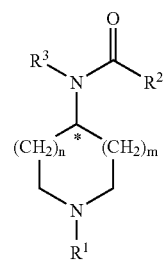

and pharmaceutically and/or veterinarily acceptable derivatives thereof, wherein $R^1$ is H, $C_{1-6}$alkyl, —C(X)Y, $C_{3-8}$cycloalkyl, aryl, het, aryl-$C_{1-4}$alkyl or het-$C_{1-4}$alkyl, wherein the cycloalkyl, aryl or het groups are optionally substituted by at least one substituent independently selected from $C_{1-8}$alkyl, $C_{1-8}$alkoxy, OH, halo, $CF_3$, $OCF_3$, $SCF_3$, hydroxy-$C_{1-6}$alkyl, $C_{1-4}$alkoxy-$C_{1-6}$alkyl and $C_{1-4}$alkyl-S—$C_{1-4}$alkyl; $R^2$ is aryl or heteroaryl, each optionally substituted by at least one substituent independently selected from $C_{1-8}$alkyl, $C_{1-8}$alkoxy, OH, halo, $CF_3$, $OCF_3$, $SCF_3$, hydroxy-$C_{1-6}$alkyl, $C_{1-4}$alkoxy-$C_{1-6}$alkyl and $C_{1-4}$alkyl-S—$C_{1-4}$alkyl; $R^3$ is $C_{1-6}$alkyl, $C_{3-8}$cycloalkyl, $C_{3-8}$cycloalkyl-$C_{1-6}$alkyl, aryl, het, aryl-$C_{1-4}$alkyl or het-$C_{1-4}$alkyl, wherein the cycloalkyl, aryl or het groups are optionally substituted by at least one substituent independently selected from $C_{1-6}$alkyl, $C_{1-8}$alkoxy, OH, halo, $CF_3$, $OCF_3$, $SCF_3$, hydroxy-$C_{1-6}$alkyl, $C_{1-4}$alkoxy —$C_{1-6}$alkyl and $C_{1-4}$alkyl-S—$C_{1-4}$alkyl; X is S or O; Y is H, $C_{1-6}$alkyl, aryl, het, aryl-$C_{1-4}$alkyl or het-$C_{1-4}$alkyl; and n is 1 or 2, provided that when n is 1, m is 0 or 1 and when n is 2, m is 0, wherein if m is 0, then * represents a chiral center. The compounds of the invention exhibit activity as both serotonin and noradrenaline re-uptake inhibitors and therefore have utility in a variety of therapeutic areas, for example urinary incontinence.

13 Claims, No Drawings

OTHER PUBLICATIONS

Schaper et al. "Preparation of nicotine acid . . . " Ca 138:282806 (2003).*
Atkinson et al. "Pyrazolecarboximades . . . " CA 138:368888 (2003).*
Zhou et al. "Synthesos of . . . " CA 139:68991 (1003).*
Kadow et al. "Preparation of indole . . . " CA 139:197364 (2003).*
Wilbraham "organic and biological cahemistry" p. 250-251 (1985).*
Farina et al. "Quinoline derivatives . . . " Ca 124:232269 (1996).*
Moragues, J. et al., Dopaminergic Activity in a Series of NSubstituted 2-Aminopyrimidines, Farmaco, Ed. Sci., vol. 35, 951-964 (1980).

* cited by examiner

COMPOUNDS

This application claims priority to U.S. Provisional Application Ser. No. 60/493,126, filed Aug. 6, 2003, which claims priority to British Application Serial No. GB 0314048.0, filed Jun. 17, 2003.

This invention relates to novel amide compounds which inhibit monoamine re-uptake, to processes for their preparation, to pharmaceutical compositions containing them and to their use in medicine.

The compounds of the invention exhibit activity as both serotonin and noradrenaline re-uptake inhibitors and therefore have utility in a variety of therapeutic areas. For example, the compounds of the invention are of use in the treatment of disorders in which the regulation of monoamine transporter function is implicated; more particularly disorders in which inhibition of re-uptake of serotonin or noradrenaline is implicated; and especially disorders in which inhibition of both serotonin and noradrenaline is implicated, such as urinary incontinence.

According to a first aspect, the invention provides a compound of formula (I),

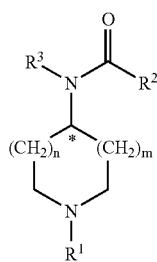

I and pharmaceutically and/or veterinarily acceptable derivatives thereof, wherein $R^1$ is H, $C_{1-6}$alkyl, —C(X)Y, $C_{3-8}$cycloalkyl, aryl, het, aryl-$C_{1-4}$alkyl, or het-$C_{1-4}$alkyl, wherein the cycloalkyl, aryl or het groups are optionally substituted by at least one substituent independently selected from $C_{1-8}$alkyl, $C_{1-8}$alkoxy, OH, halo, $CF_3$, $OCF_3$, $SCF_3$, hydroxy-$C_{1-6}$alkyl, $C_{1-4}$alkoxy-$C_{1-6}$alkyl and $C_{1-4}$alkyl-S—$C_{1-4}$alkyl;

$R^2$ is aryl or heteroaryl optionally substituted by at least one substituent independently selected from $C_{1-8}$alkyl, $C_{1-8}$alkoxy, OH, halo, $CF_3$, $OCF_3$, $SCF_3$, hydroxy-$C_{1-16}$alkyl, $C_{1-4}$alkoxy-$C_{1-6}$alkyl and $C_{1-4}$alkyl-S—$C_{1-4}$alkyl;

$R^3$ is $C_{1-6}$alkyl, $C_{3-8}$cycloalkyl, $C_{3-8}$cycloalkyl-$C_{1-6}$alkyl, aryl, het, aryl-$C_{1-4}$alkyl or het-$C_{1-4}$alkyl, wherein the cycloalkyl, aryl or het groups are optionally substituted by at least one substituent independently selected from $C_{1-6}$alkyl, $C_{1-6}$alkoxy, OH, halo, $CF_3$, $OCF_3$, $SCF_3$, hydroxy-$C_{1-6}$alkyl, $C_{1-4}$alkoxy-$C_{1-6}$alkyl and $C_{1-4}$alkyl-S—$C_{1-4}$alkyl;

X is S or O;

Y is H, $C_{1-6}$alkyl, $C_{1-6}$alkoxy, aryl, het, aryl-$C_{1-4}$alkyl or het-$C_{1-4}$alkyl;

n is 1 or 2, provided that when n is 1, m is 0 or 1 and when n is 2, m is 0, wherein if m is 0, then * represents a chiral centre;

aryl is phenyl, naphthyl, anthracyl or phenanthryl;

heteroaryl is an aromatic 5- or 6-membered heterocycle which contains at least one N, O or S heteroatom, optionally fused to an aryl group; and het is an aromatic or non-aromatic 4-, 5- or 6-membered heterocycle which contains at least one N, O or S heteroatom, optionally fused to a 5 or 6-membered carbocyclic group or a second 4-, 5- or 6-membered heterocycle which contains at least one N, O or S heteroatom.

In an embodiment of the invention, $R^1$ is H and $R^2$, $R^3$ and m are as defined above.

In a further embodiment of the invention, m is 0 and $R^1$, $R^2$ and $R^3$ are as defined above. Where m is 0, * represents the R or S enantiomeric configuration. Thus, in a further embodiment, m is 0, $R^1$, $R^2$ and $R^3$ are as defined above and * represents the S enantiomer.

In a still further embodiment, $R^1$, $R^3$ and m are as defined above and $R^2$ is phenyl, naphthyl or quinolinyl, each optionally substituted by at least one substituent independently selected from $C_{1-8}$alkyl, $C_{1-8}$alkoxy, OH, halo, $CF_3$, $OCF_3$, $SCF_3$, hydroxy-$C_{1-6}$alkyl, $C_{1-4}$alkoxy-$C_{1-6}$alkyl and $C_{1-4}$alkyl-S—$C_{1-4}$alkyl. In a yet further embodiment, the substituents may be selected from halo, OH, $C_{1-4}$alkyl, $C_{1-4}$alkoxy and $CF_3$. Optionally, the phenyl, naphthyl or quinolinyl group may be substituted by one, two or three substituents, each independently selected from halo, OH and $C_{1-4}$alkyl. In a further embodiment, $R^2$ is phenyl and is substituted by two substituents selected from chloro, fluoro, OH and $C_{1-4}$alkyl. In a still further embodiment, $R^2$ is dichlorophenyl.

In a yet further embodiment, $R^1$, $R^2$ and m are as defined above and $R^3$ is $C_{1-6}$alkyl, $C_{3-8}$cycloalkyl or $C_{3-8}$cycloalkyl-$C_{1-6}$alkyl. In a further embodiment, $R^3$ is $C_{1-6}$alkyl, $C_{3-6}$cycloalkyl or $C_{3-6}$cycloalkyl-$C_{1-4}$alkyl.

In a yet further embodiment of the invention, there is provided a compound of Formula II

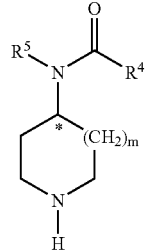

II and pharmaceutically and/or veterinarily acceptable derivatives thereof, wherein $R^4$ is phenyl, naphthyl, or quinolinyl, each optionally substituted by at least one substituent independently selected from $C_{1-8}$alkyl, $C_{1-8}$alkoxy, OH, halo, $CF_3$, $OCF_3$, $SCF_3$, hydroxy —$C_{1-6}$alkyl, $C_{1-4}$alkoxy-$C_{1-6}$alkyl, and $C_{1-4}$alkyl-S—$C_{1-4}$alkyl;

$R^5$ is $C_{1-6}$alkyl, $C_{3-8}$cycloalkyl, $C_{3-8}$cycloalkyl-$C_{1-6}$alkyl, aryl or aryl-$C_{1-4}$alkyl wherein the cycloalkyl and aryl groups are optionally substituted by at least one substituent each independently selected from $C_{1-6}$alkyl, $C_{1-6}$alkoxy, OH, halo, $CF_3$, $OCF_3$, $SCF_3$, hydroxy-$C_{1-6}$alkyl, $C_{1-4}$alkoxy-$C_{1-6}$alkyl, and $C_{1-4}$alkyl-S-$C_{1-4}$alkyl; and m is 0 or 1, wherein if m is 0, then * represents the R or S enantiomer.

In a further embodiment, $R^5$ and m are as defined above and $R^4$ is phenyl, 1-naphthyl or 2-naphthyl, each optionally substituted by at least one substituent independently selected from $C_{1-8}$alkyl, $C_{1-8}$alkoxy, OH, halo, $CF_3$, $OCF_3$, $SCF_3$, hydroxy-$C_{1-16}$alkyl, $C_{1-4}$alkoxy-$C_{1-6}$alkyl and $C_{1-4}$alkyl-S—$C_{1-4}$alkyl. The substituents may optionally be selected from $C_{1-6}$alkyl, $C_{1-6}$alkoxy, OH, halo and $CF_3$. The phenyl or naphthyl groups may be substituted by one, two or three substituents. In an embodiment, the phenyl or naphthyl groups are substituted by two substituents. In a further embodiment, the phenyl or naphthyl groups are substituted by two substituents independently selected from chloro, fluoro, $C_{1-4}$alkyl and OH. In a yet further embodiment, the phenyl or naphthyl groups are substituted by two chloro groups.

In a still further embodiment, $R^4$ and m are as defined above and $R^5$ is $C_{1-6}$alkyl, $C_{3-6}$cycloalkyl or $C_{3-6}$cycloalkyl-$C_{1-4}$alkyl.

In a yet still further embodiment, $R^4$ and $R^5$ are as defined above and m is 0. In this embodiment, * represents the R or S enantiomer. In a further embodiment, m is 0 and * represents the S enantiomer.

In a still further embodiment, there is provided a compound of Formula III

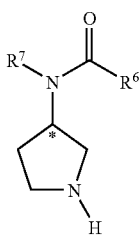

and pharmaceutically and/or veterinarily acceptable derivatives thereof, wherein $R^6$ is phenyl, naphthyl or quinolinyl, each optionally substituted by at least one substituent independently selected from halo, OH, $C_{1-6}$alkyl, $C_{1-6}$alkoxy and $CF_3$;

$R^7$ is $C_{1-6}$alkyl, $C_{3-6}$cycloalkyl, $C_{3-6}$cycloalkyl-$C_{1-4}$alkyl, aryl or aryl-$CH_2$—, wherein the cycloalkyl and aryl groups are optionally substituted by at least one group each independently selected from halo, OH, $C_{1-4}$alkyl, $C_{1-4}$alkoxy and $CF_3$; and

* represents the R or S enantiomer.

In a further embodiment, $R^7$ and * are as defined above and $R^6$ is phenyl, 1-naphthyl or 2-naphthyl, each optionally substituted by at least one substituent independently selected from halo, OH, $C_{1-6}$alkyl, $C_{1-6}$alkoxy and $CF_3$. The substituents may optionally be selected from chloro, fluoro, $C_{1-4}$alkyl, OMe and OH. The phenyl and naphthyl groups may be substituted by one, two or three substituents. In a further embodiment, the phenyl and naphthyl groups are substituted by one, two or three halo groups independently selected from fluoro and chloro.

In a further embodiment, $R^7$ and * are as defined above and $R^7$ is $C_{1-6}$alkyl, $C_{3-6}$cycloalkyl or $C_{3-6}$cycloalkyl-$C_{1-4}$alkyl. In a still further embodiment, $R^7$ is $C_{1-6}$alkyl, optionally a $C_{3-6}$alkyl. Where $R^7$ is a $C_{3-6}$alkyl, it may be a branched $C_{3-6}$alkyl.

In a yet further embodiment, $R^6$ and $R^7$ are as defined above and * represents the S enantiomer.

In a still yet further embodiment, there is provided a compound of Formula IV:

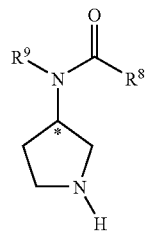

and pharmaceutically and/or veterinarily acceptable derivatives thereof, wherein
$R^8$ is phenyl, optionally substituted by 1-3 halo substituents;
$R^9$ is $C_{1-6}$alkyl; and
* represents the R or S enantiomer.

Optionally, $R^8$ is dichlorophenyl, $R^9$ is $C_{3-4}$ branched alkyl and * represents the S enantiomer. $R^9$ may be an isobutyl group.

In a further embodiment, the invention provides a compound selected from:
2,3-Dichloro-N-isobutyl-N-[(3S)-pyrrolidin-3-yl]benzamide;
2,4-Dichloro-N-isobutyl-N-[(3S)-pyrrolidin-3-yl]benzamide;
2-Chloro-3-methyl-N-isobutyl-N-[(3S)-pyrrolidin-3-yl]benzamide;
3-Fluoro-2-methyl-N-isobutyl-N-[(3S)-pyrrolidin-3-yl]benzamide;
3-Methoxy-2-methyl-N-isobutyl-N-[(3S)-pyrrolidin-3-yl]benzamide;
3-Chloro-N-isobutyl-N-[(3S)-pyrrolidin-3-yl]benzamide;
4-Chloro-N-isobutyl-N-[(3S)-pyrrolidin-3-yl]benzamide;
3,4-Dichloro-N-isobutyl-N-[(3S)-pyrrolidin-3-yl]benzamide;
N-(2-Naphthylmethyl)-N-[(3S)-pyrrolidin-3-yl]benzamide;
N-(2-Naphthyl methyl)-N-[(3R)-pyrrolidin-3-yl]benzamide;
N-Isobutyl-N-[(3S)-pyrrolidin-3-yl]-2-naphthamide;
N-Butyl-N-[(3S)-pyrrolidin-3-yl]-n-naphthamide;
4-Chloro-N-(3,4-dichlorobenzyl)-N-[(3R)-pyrrolidin-3-yl]benzamide;
4-Chloro-N-(2,3-dichlorobenzyl)-N-[(3R)-pyrrolidin-3-yl]benzamide;

and pharmaceutically and/or veterinarily acceptable derivatives thereof.

Further, non-limiting, examples of compounds within the scope of the invention include:
N-Pyrrolidin-3-yl-N-(5,6,7,8-tetrahydro-naphthalen-1-ylmethyl)-benzamide;
N-(2,4-Dichloro-benzyl)-N-pyrrolidin-3-yl-benzamide;
N-(3-Chloro-4-methyl-benzyl)-2-fluoro-N-pyrrolidin-3-yl-benzamide;
Naphthalene-2-carboxylic acid butyl-pyrrolidin-3-yl-amide;
Naphthalene-2-carboxylic acid isobutyl-pyrrolidin-3-yl-amide;
Naphthalene-2-carboxylic acid (2,2-dimethyl-propyl)-pyrrolidin-3-yl-amide;
3-Chloro-N-isobutyl-4-methyl-N-pyrrolidin-3-yl-benzamide;

N-isobutyl-2,3-dimethyl-N-pyrrolidin-3-yl-benzamide;
3-Chloro-N-(2,2-dimethyl-propyl)-2-methyl-N-pyrrolidin-3-yl-benzamide;
2-Chloro-4-fluoro-N-isobutyl-N-pyrrolidin-3-yl-benzamide;
2-Chloro-N-isobutyl-N-pyrrolidin-3-yl-benzamide;
3-Chloro-2-fluoro-N-isobutyl-N-pyrrolidin-3-yl-benzamide;
3-Chloro-4-fluoro-N-isobutyl-N-pyrrolidin-3-yl-benzamide;
N-Butyl-2,4-dichloro-N-pyrrolidin-3-yl-benzamide;
2,4-Dichloro-N-cyclobutylmethyl-N-pyrrolidin-3-yl-benzamide;
2,4-Dichloro-N-cyclopentylmethyl-N-pyrrolidin-3-yl-benzamide;
2,4-Dichloro-N-(2,2-dimethyl-propyl)-2-methyl-N-pyrrolidin-3-yl-benzamide;
2,4-Dichloro-N-(2-ethyl-butyl)-N-pyrrolidin-3-yl-benzamide;
2,4-Dichloro-N-(3-methyl-butyl)-N-pyrrolidin-3-yl-benzamide;
2,3,4-Trichloro-N-isobutyl-N-pyrrolidin-3-yl-benzamide;
2,4-Dichloro-N-(2-cyclopropyl-ethyl)-N-pyrrolidin-3-yl-benzamide;
Naphthalene-1-carboxylic acid isobutyl-pyrrolidin-3-yl-amide;
2,4-Dichloro-5-fluoro-N-isobutyl-N-pyrrolidin-3-yl-benzamide;
2,3-Dichloro-N-(2,2-dimethyl-propyl)-N-pyrrolidin-3-yl-benzamide;
2,3-Dichloro-N-(3-methyl-butyl)-N-pyrrolidin-3-yl-benzamide;
2,3-Dichloro-N-cyclobutylmethyl-N-pyrrolidin-3-yl-benzamide;
2,3-Dichloro-N-cyclopentyl-N-pyrrolidin-3-yl-benzamide;
3,4-Dichloro-N-cyclopentyl-N-pyrrolidin-3-yl-benzamide;
2,3-Dichloro-N-(1,2-dimethyl-propyl)-N-pyrrolidin-3-yl-benzamide;
2,4-Dichloro-N-(1,2-dimethyl-propyl)-N-pyrrolidin-3-yl-benzamide;
2,3-Dichloro-N-cyclohexyl-N-pyrrolidin-3-yl-benzamide;
2,4-Dichloro-N-cyclopentyl-N-pyrrolidin-3-yl-benzamide;
3,4-Dichloro-N-cyclopentyl-N-pyrrolidin-3-yl-benzamide;
Naphthalene-1-carboxylic acid sec-butyl-pyrrolidin-3-yl-amide;
N-sec-Butyl-2,3-dichloro-N-pyrrolidin-3-yl-benzamide;
N-sec-Butyl-2,4-dichloro-N-pyrrolidin-3-yl-benzamide;
2,3-Dichloro-N-(1-ethyl-propyl)-N-pyrrolidin-3-yl-benzamide;
2,4-Dichloro-N-(1-ethyl-propyl)-N-pyrrolidin-3-yl-benzamide;
Naphthalene-1-carboxylic acid (1-ethyl-propyl)-pyrrolidin-3-yl-amide;
2,3-Dichloro-N-cyclobutyl-N-pyrrolidin-3-yl-benzamide;
2,4-Dichloro-N-cyclobutyl-N-pyrrolidin-3-yl-benzamide;
2,4-Dichloro-N-cyclopentyl-N-pyrrolidin-3-yl-benzamide;
2,3-Dichloro-N-pyrrolidin-3-yl-N-(1,2,2-trimethyl-propyl)-benzamide;
N-tert-Butyl-2,3-dichloro-N-pyrrolidin-3-yl-benzamide;
Naphthalene-1-carboxylic acid cyclopentyl-pyrrolidin-3-yl-amide;
2,3-Dichloro-N-phenyl-N-pyrrolidin-3-yl-benzamide;
3,4-Dichloro-N-(2,2-dimethyl-propyl)-2-methyl-N-pyrrolidin-3-yl-benzamide;
3-Chloro-N-isobutyl-2-methyl-N-pyrrolidin-3-yl-benzamide;
N-Butyl-2,3-dichloro-N-pyrrolidin-3-yl-benzamide;
N-Butyl-3,4-dichloro-N-pyrrolidin-3-yl-benzamide;
Naphthalene-2-carboxylic acid cyclobutylmethyl-pyrrolidin-3-yl-amide;
Naphthalene-1-carboxylic acid cyclobutylmethyl-pyrrolidin-3-yl-amide;
3,4-Dichloro-N-cyclobutylmethyl-N-pyrrolidin-3-yl-benzamide;
4-Chloro-N-isobutyl-2-methoxy-N-pyrrolidin-3-yl-benzamide;
4-Chloro-N-isobutyl-3-methyl-N-pyrrolidin-3-yl-benzamide;
2,4-Dichloro-N-isobutyl-3-methyl-N-pyrrolidin-3-yl-benzamide;
Naphthalene-1-carboxylic acid (3-methyl-butyl)-pyrrolidin-3-yl-amide;
Naphthalene-1-carboxylic acid (2,2-dimethyl-propyl)-pyrrolidin-3-yl-amide;
3,4-Dichloro-N-(3-methyl-butyl)-N-pyrrolidin-3-yl-benzamide;
2,3-Dichloro-N-(4-fluoro-phenyl)-N-pyrrolidin-3-yl-benzamide;
2,4-Dichloro-N-(4-fluoro-phenyl)-N-pyrrolidin-3-yl-benzamide;
Naphthalene-1-carboxylic acid (4-fluoro-phenyl)-pyrrolidin-3-yl-amide;
N-Butyl-2,3,4-trichloro-N-pyrrolidin-3-yl-benzamide;
2,3,4-Trichloro-N-cyclobutylmethyl-N-pyrrolidin-3-yl-benzamide;
N-Pyrrolidin-3-yl-N-(3-trifluoromethyl-benzyl)-benzamide;
2,4-Dichloro-N-phenyl-N-pyrrolidin-3-yl-benzamide;
3,4-Dichloro-N-phenyl-N-pyrrolidin-3-yl-benzamide;
2,3,4-Trichloro-N-(2,2-dimethyl-propyl)-N-pyrrolidin-3-yl-benzamide;
Naphthalene-1-carboxylic acid phenyl-pyrrolidin-3-yl-amide;
2,3,4-Trichloro-N-(2-cyclopropyl-ethyl)-N-pyrrolidin-3-yl-benzamide;
2,3-Dichloro-N-(2-cyclopropyl-ethyl)-N-pyrrolidin-3-yl-benzamide;
2-Bromo-4-chloro-N-isobutyl-N-pyrrolidin-3-yl-benzamide;
4-Chloro-2-ethoxy-N-isobutyl-N-pyrrolidin-3-yl-benzamide;
3-Bromo-4-chloro-N-isobutyl-N-pyrrolidin-3-yl-benzamide;
3,4-Dichloro-N-isobutyl-2-methyl-N-pyrrolidin-3-yl-benzamide;
2,4-dichloro-3-fluoro-N-isobutyl-N-[pyrrolidin-3-yl]benzamide;
2,3-dichloro-4-fluoro-N-isobutyl-N-[pyrrolidin-3-yl]benzamide;
2,3-dichloro-5-fluoro-N-isobutyl-N-[pyrrolidin-3-yl]benzamide;
2,4,5-trichloro-N-isobutyl-N-[pyrrolidin-3-yl]benzamide;
2,5-dichloro-N-isobutyl-N-[pyrrolidin-3-yl]benzamide;
2,5-dichloro-4-fluoro-N-isobutyl-N-[pyrrolidin-3-yl]benzamide;
2,3,5-trichloro-N-isobutyl-N-[pyrrolidin-3-yl]benzamide;
2,3-dichloro-6-fluoro-N-isobutyl-N-[pyrrolidin-3-yl]benzamide;
3,4-dichloro-6-fluoro-N-isobutyl-N-[pyrrolidin-3-yl]benzamide;
3,4-dichloro-2-fluoro-N-isobutyl-N-[pyrrolidin-3-yl]benzamide;
2-chloro-3,6-difluoro-N-isobutyl-N-[pyrrolidin-3-yl]benzamide;

2,4-Dichloro-5-fluoro-N-isobutyl-N-[(3S)-pyrrolidin-3-yl] benzamide;

and pharmaceutically and/or veterinarily acceptable derivatives thereof.

By pharmaceutically and/or veterinarily acceptable derivative it is meant any pharmaceutically or veterinarily acceptable salt, solvate, ester or amide, or salt or solvate of such ester or amide, of the compounds of formula (I), (II), (III) or (IV) or any other compound which upon administration to the recipient is capable of providing (directly or indirectly) a compound of formula (I), (II), (III) or (IV) or an active metabolite or residue thereof.

For pharmaceutical or veterinary use, the salts referred to above will be the pharmaceutically or veterinarily acceptable salts, but other salts may find use, for example in the preparation of compounds of formula (I), (II), (III) or (IV) and the pharmaceutically or veterinarily acceptable salts thereof.

The aforementioned pharmaceutically or veterinarily acceptable salts include the acid addition and base salts thereof.

Suitable acid addition salts are formed from acids which form non-toxic salts. Examples include the acetate, aspartate, benzoate, besylate, bicarbonate/carbonate, bisulphate/sulphate, camsylate, citrate, edisylate, hemiedisylate, esylate, fumarate, gluceptate, gluconate, glucuronate, hibenzate, hydrochloride/chloride, hydrobromide/bromide, hydroiodide/iodide, isethionate, lactate, malate, maleate, malonate, mesylate, methylsulphate, 2-napsylate, nicotinate, nitrate, orotate, pamoate, phosphate/hydrogen phosphate/dihydrogen phosphate, saccharate, stearate, succinate, tartrate and tosylate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula (I), (II), (III) or (IV) may be readily prepared by mixing together solutions of the compound and the desired acid or base, as appropriate. The salt may precipitate from solution and be collected by filtration or may be recovered by evaporation of the solvent. The degree of ionisation in the salt may vary from completely ionised to almost non-ionised.

Pharmaceutically acceptable solvates in accordance with the invention include hydrates and solvates of the compounds of formula (I), (II), (III) or (IV).

Also within the scope of the invention are complexes such as clathrates, drug-host inclusion complexes wherein, in contrast to the aforementioned solvates, the drug and host are present in stoichiometric or non-stoichiometric amounts. Also included in this invention are complexes of the pharmaceutical drug which contain two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

The compounds of formula (I), (II), (III) or (IV) may be modified to provide pharmaceutically or veterinarily acceptable derivatives thereof at any of the functional groups in the compounds. Examples of such derivatives are described in: Drugs of Today, Volume 19, Number 9, 1983, pp 499-538; Topics in Chemistry, Chapter 31, pp 306-316; and in "Design of Prodrugs" by H. Bundgaard, Elsevier, 1985, Chapter 1 (the disclosures in which documents are incorporated herein by reference) and include: esters, carbonate esters, hemi-esters, phosphate esters, nitro esters, sulfate esters, sulfoxides, amides, sulphonamides, carbamates, azo-compounds, phosphamides, glycosides, ethers, acetals and ketals.

It will be further appreciated by those skilled in the art, that certain moieties, known in the art as "pro-moieties", for example as described by H. Bundgaard in "Design of Prodrugs" (ibid) may be placed on appropriate functionalities when such functionalities are present within compounds of the invention.

The compounds of formula (I), (II), (III) or (IV) may contain one or more chiral centres, by virtue of the asymmetric carbon atom defined by certain meanings of $R^1$ to $R^9$ (e.g. s-butyl), or the value of the integer m. Such compounds exist in a number of stereoisomeric forms (e.g. in the form of a pair of optical isomers, or enantiomers). It is to be understood that the present invention encompasses all isomers of the compounds of the invention, including all geometric, tautomeric and optical forms, and mixtures thereof (e.g. tautomeric or racemic mixtures).

The compounds of the invention may exist in one or more tautomeric forms. All tautomers and mixtures thereof are included in the scope of the present invention. For example, a claim to 2-hydroxypyridinyl would also cover its tautomeric form α-pyridonyl.

It is to be understood that the present invention includes radiolabelled compounds of formula (I), (II), (III) or (IV).

The compounds of formula (I), (II), (III) or (IV) and their pharmaceutically and veterinarily acceptable derivatives thereof may also be able to exist in more than one crystal form, a characteristic known as polymorphism. All such polymorphic forms ("polymorphs") are encompassed within the scope of the invention. Polymorphism generally can occur as a response to changes in temperature or pressure or both, and can also result from variations in the crystallisation process. Polymorphs can be distinguished by various physical characteristics, and typically the x-ray diffraction patterns, solubility behaviour, and melting point of the compound are used to distinguish polymorphs.

Unless otherwise indicated, any alkyl group may be straight or branched and is of 1 to 8 carbon atoms, such as 1 to 6 carbon atoms or 1 to 4 carbon atoms, for example a methyl, ethyl, n-propyl, i-propyl, n-butyl, i-butyl, s-butyl or t-butyl group. Where the alkyl group contains more than one carbon atom, it may be unsaturated. Thus, the term $C_{1-6}$alkyl includes $C_{2-6}$alkenyl and $C_{2-6}$alkynyl. Similarly, the term $C_{1-8}$alkyl includes $C_{2-8}$alkenyl and $C_{2-8}$alkynyl, and the term $C_{1-4}$alkyl includes $C_{2-4}$alkenyl and $C_{2-4}$alkynyl.

The term halogen is used to represent fluorine, chlorine, bromine or iodine.

Unless otherwise indicated, the term het includes any aromatic, saturated or unsaturated 4-, 5- or 6- membered heterocycle which contains up to 4 heteroatoms selected from N, O and S. Examples of such heterocyclic groups included furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, dioxanyl, morpholino, dithianyl, thiomorpholino, pyridazinyl, pyrimidinyl, pyrazinyl, piperazinyl, sulfolanyl, tetrazolyl, triazinyl, azepinyl, oxazapinyl, thiazepinyl, diazepinyl and thiazolinyl. In addition, the term heterocycle includes fused heterocyclyl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazdinyl, benzothiazolyl, phthalimido, benzodiazepinyl, indolyl and isoindolyl. The terms het, heterocyclyl and heterocyclic should be similarly construed.

For the avoidance of doubt, unless otherwise indicated, the term substituted means substituted by one or more defined groups. In the case where groups may be selected from a number of alternative groups, the selected groups may be the same or different. Further, the term independently means that where more than one substituent is selected from a number of possible substituents, those substituents may be the same or different.

Hereinafter, the compounds of formula (I), (II), (III) and (IV) and their pharmaceutically and veterinarily acceptable derivatives, the radiolabelled analogues of the foregoing, the isomers of the foregoing, and the polymorphs of the foregoing, are referred to as "compounds of the invention".

In one embodiment of the invention, the compounds of the invention are the pharmaceutically and veterinarily acceptable derivatives of compounds of formula (I), (II), (III) or (IV), such as the pharmaceutically or veterinarily acceptable salts or solvates of compounds of formula (I), (II), (III) or (IV), (e.g. pharmaceutically or veterinarily acceptable salts of compounds of formula (I), (II), (III) or (IV)).

In a still further embodiment of the invention, there is provided a compound of the invention which is an inhibitor of serotonin and/or noradrenaline monoamine re-uptake, having SRI or NRI $IC_{50}$ values of 200 nM or less. In a further embodiment, the compound has SRI and/or NRI $IC_{50}$ values of 100 nM or less. In a yet further embodiment, the compound has SRI or NRI $IC_{50}$ values of 50 nM or less. In a still further embodiment, the compound has SRI and NRI $IC_{50}$ values of 50 nM or less. In a still yet further embodiment, the compound has SRI and NRI $IC_{50}$ values of 25 nM or less.

According to Scheme 1, compounds of Formula (V) may be prepared from compounds of Formula (VI) by reaction with an aldehyde $R^{3'}CHO$, followed by reaction with an acid or acid chloride $R^2COX$ (where X is OH or halo) and deprotection.

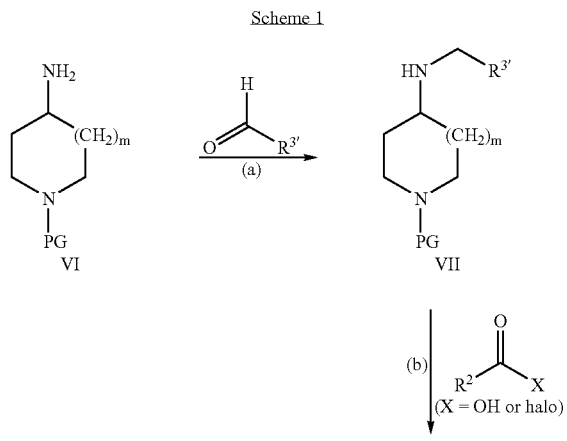

Scheme 1

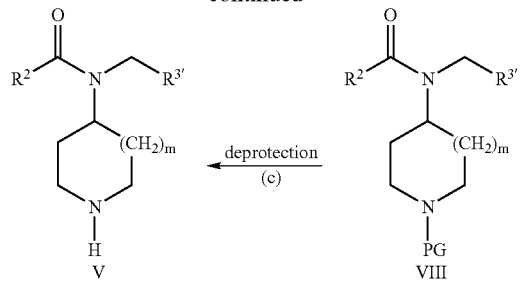

-continued

In the above scheme, $R^2$ and m are as defined above, PG is a protecting group and the moiety $-CH_2R^{3'}$ satisfies the definition of $R^3$.

(a)—Reductive Amination

The reaction of the 1° amine (VI) with the aldehyde to form the 2° amine (VII) is a reductive amination reaction, in which the dehydration of the amine and the aldehyde is followed by reduction of the formed imine by a metal hydride reagent or hydrogenation, in a suitable solvent at room temperature.

In this reaction, equimolar amounts of amine and aldehyde are typically treated with either sodium triacetoxyborohydride (STAB), $NaCN(BH)_3$ or $NaBH_4$, in a suitable solvent (e.g. DCM, THF) at room temperature for 1 to 24 hours. Alternatively, an excess of a reducing agent (e.g. $NaBH_4$, $LiAlH_4$, STAB) in a suitable solvent (e.g. THF, MeOH, EtOH) is added after the amine and aldehyde have been mixed for 1-18 hours, optionally in the presence of a drying agent (e.g. molecular sieve) or with the removal of water using Dean-Stark apparatus with a suitable solvent (e.g. toluene, xylene). A further alternative involves catalytic hydrogenation in the presence of a palladium or nickel catalyst (e.g. Pd/C, Raney® Ni) under an atmosphere of $H_2$, optionally at elevated temperature and pressure, in a suitable solvent (e.g. EtOH).

A more specific example of the reductive amination involves treatment of the aldehyde with the amine in the presence of either 10% Pd/C, optionally in the presence of triethylamine, in ethanol under about 415 kPa (about 60 psi) of hydrogen at room temperature for 18 hours, or an excess of sodium borohydride in methanol at room temperature for 6 hours.

(b)—Amide Formation

The formation of a peptide linkage between the acid or acid halide and the amine (VII) may be undertaken by using either:

(i) the acyl halide and the amine (VII), with an excess of acid acceptor in a suitable solvent, or (ii) the acid, optionally with a conventional coupling agent, and the amine (VII), optionally in the presence of a catalyst, with an excess of acid acceptor in a suitable solvent.

Examples of such reaction are as follows:

(i) An acid chloride (optionally generated in-situ) is reacted with an excess of the amine (VII), optionally with an excess of 3° amine such as $Et_3N$, Hünig's base or NMM, in DCM or dioxane, optionally at elevated temperature for 1 to 24 hrs;

(ii) An acid, WSCDI/DCCI/TBTU and HOBT/HOBT is reacted with an excess of amine (VII) and an excess of NMM, Et$_3$N, Hünig's base in THF, DCM or EtOAc, at rt. for 4 to 48 hrs; or (iii) An acid and PYBOP®/PyBrOP®/Mukaiyama's reagent is reacted with an excess of amine(VII) and an excess of NMM, Et$_3$N, Hünig's base in THF, DCM or EtOAc, at rt. for 4 to 24 hrs.

Where the acid halide is an acid chloride (i.e. X=Cl), this may be generated in-situ by standard methodology and then reacted with the amine (VII) and triethylamine in dichloromethane at 70° C. for 90 minutes.

(c)—Deprotection

Where PG is a suitable amine-protecting group, preferably BOC, trifluoroacetate or benzyl, the removal of PG from (VIII), to form the unprotected amine (V), is performed by a method selective to the protecting group as detailed in "Protective Groups in Organic Synthesis", 3$^{rd}$ edition, by T W Greene and P G M Wuts. John Wiley and Sons, Inc., 1999, incorporated herein by reference.

Examples of such deprotection reactions are as follows:

When PG is BOC, the deprotection involves treatment of (VIII) with an excess of strong acid (e.g. HCl, TFA) at room temperature in a suitable solvent (e.g. DCM, EtOAc, dioxan).

When PG is trifluoroactetate, the deprotection involves treatment of (VIII) with a base (e.g. K$_2$CO$_3$, Na$_2$CO$_3$, NH$_3$, Ba(OH)$_2$) in an alcoholic solvent (e.g. MeOH, EtOH), optionally with water and optionally at elevated temperature.

When PG is Bz, the deprotection involves either transfer hydrogenation with a transition metal or transition metal salt hydrogenation catalyst (e.g. Pd/C, Pd(OH)$_2$) in the presence of a hydrogen donor (e.g. NH$_4$$^+$HCO$_2$$^-$) in a polar solvent (e.g. tetrahydrofuran, ethanol, methanol) optionally at elevated temperature and/or pressure, or catalytic hydrogenation in the presence of a palladium or nickel catalyst (e.g. Pd/C, Raney® Ni) under an atmosphere of H$_2$, optionally at elevated temperature and pressure, in a suitable solvent.

More specifically:

When PG is BOC, the deprotection involves treatment with either an excess of 4M hydrochloric acid in dioxan for 18 hours at room temperature. Or with TFA in DCM for 4.5 hours at RT.

When PG is trifluoroactetate, the deprotection involves treatment with K$_2$CO$_3$ in methanol:water mixture (5:1 to 10:1) at room temperature for 18 hours.

When PG is Bz, the deprotection involves treatment with NH$_4$$^+$HCO$_2$$^-$ and 10% Pd/C in ethanol under gentle reflux for between 6 and 20 hours.

According to Scheme 2, compounds of Formula (IX) may be prepared from compounds of Formula (VI) by reaction with R$^3$-L, where L is a leaving group, under suitable conditions. The resulting compound of Formula (IX) may then be converted to a compound of Formula (II) by amide formation and deprotection in a manner analogous to that described above in relation to Scheme 1.

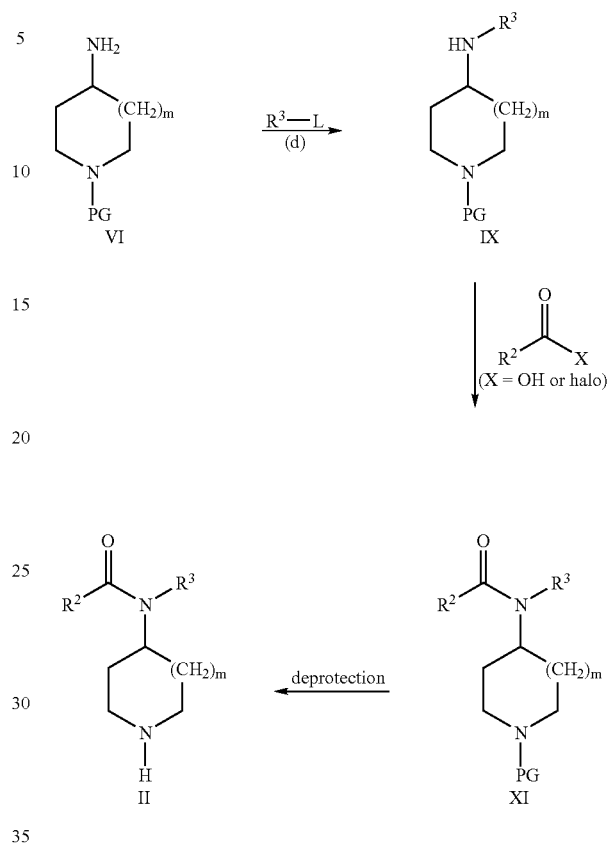

Scheme 2

In the above scheme, R$^2$, R$^3$ and m are as defined above, PG is a suitable protecting group and L is a leaving group, whose meaning will depend, inter alia, on the nature of the reaction and the specific reaction conditions employed. Suitable leaving groups will be readily apparent to the skilled person and are described in many standard organic chemistry texts, for example: "Advanced Organic Chemistry", Jerry March, Third Edition, Wiley (1985), page 587, incorporated herein by reference; they include halogen (e.g. Br) and sulfonate esters (e.g. methanesulfonate or trifluoromethanesulfonate).

Conveniently, R$^3$ is an aryl group, L is Br and reaction (d) is carried out in a suitable solvent at elevated temperatures in the presence of a palladium catalyst. Such palladium mediated aryl amination reactions are well known to those skilled in the art.

A more specific example of a process according to Scheme 2 involves the treatment of an aryl bromide with an amine of Formula (VI) in the presence of tris(dibenzylideneacetone)dipalladium, 2,2'-bis(diphenylphosphino)-1,1'-binaphthyl and sodium tert-butoxide in toluene at 100° C. for 18 hours.

According to Scheme 3, compounds of Formula (IX) may be prepared from a ketone of Formula (XII) by reaction with a primary amine R$^3$—NH$_2$ under suitable conditions. The resulting compound of Formula (IX) may then be converted to a compound of Formula (II) by amide formation and deprotection in a manner analogous to that described above in relation to Scheme 1.

Scheme 3

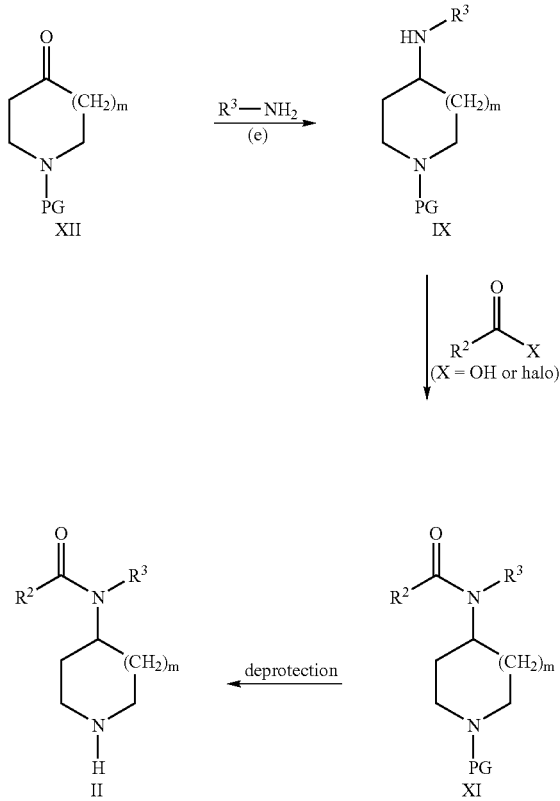

In the above scheme, $R^2$, $R^3$ and m are as defined above and PG is a suitable protecting group.

The reaction (e) of the primary amine $R^3$—$NH_2$ with the ketone (XII) may conveniently be a reductive amination reaction in which the dehydration of the amine and the ketone is followed by reduction of the resultant imine, for example by a metal hydride reagent or hydrogenation, under suitable conditions.

Conveniently, the reaction of the amine and the ketone is carried out in the presence of titanium (IV) tetraisopropoxide in THF at room temperature for 18 hours, followed by reduction by an excess of sodium borohydride in methanol at room temperature for 5 hours.

The skilled person is able to select the most appropriate synthetic route to the desired compound according to Formula (I), (II), (III) or (IV). The above schemes may of course be modified as appropriate in accordance with the common general knowledge of those skilled in the art.

For example, the skilled person will of course appreciate that the hydrogen attached to the piperidine or pyrrolidine nitrogen (depending upon the value of m) of the deprotected amide (II) or (V) can be replaced with alternative groups as desired to form a compound of Formula (I) where n is 1 and m is 0 or 1 by the use of conventional synthetic methodologies.

In addition, compounds of Formula (I) where n is 2 and m is 0 can be prepared by analogous processes to those described above using the appropriate starting materials.

It will be appreciated by those skilled in the art that one or more sensitive functional groups may need to be protected and deprotected during the synthesis of a compound of Formula (I), (II), (III) or (IV). This may be achieved by conventional techniques, for example as described in "Protective Groups in Organic Synthesis", $3^{rd}$ edition, by T W Greene and P G M Wuts. John Wiley and Sons, Inc., 1999, incorporated herein by reference, which also describes methods for the removal of such groups.

It will be apparent to those skilled in the art that certain protected derivatives of compounds of the invention, which may be made prior to a final deprotection stage, may not possess pharmacological activity as such, but may, in certain instances, be administered orally or parenterally and thereafter metabolized in the body to form compounds of the invention which are pharmacologically active. Such derivatives may therefore be described as prodrugs. Further, certain compounds of the invention may act as prodrugs of other compounds of the invention.

Thus, according to a further aspect of the invention, there is provided a process for preparing compounds of Formula (I), (II), (III) or (IV), which comprises reacting a compound of formula (X):

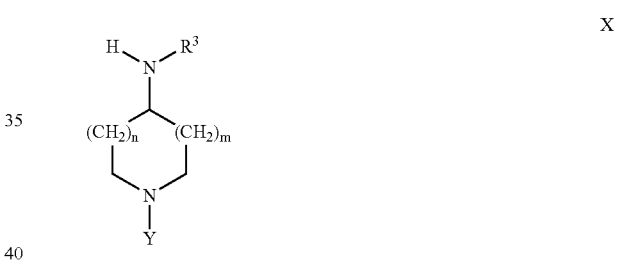

wherein $R^3$, n and m are as defined above and Y is $R^1$ or a protecting group, with an acid or acyl halide: $R^2COX$, wherein X is OH or halo, and deprotecting if necessary.

Where $R^3$ includes a methylene moiety which is directly bonded to the nitrogen atom, then the compound of Formula (X) may be prepared by reacting a compound of Formula (XXI) with an aldehyde $R^{3'}CHO$ (wherein —$CH_2R^{3'}$ satisfies the definition of $R^3$).

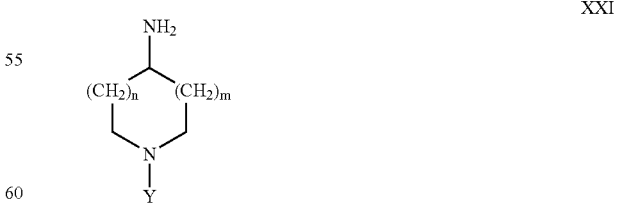

Alternatively, the compound of Formula (X) may be prepared by reacting a compound of Formula (XXI) with a compound $R^3$-L, where L is a leaving group, optionally selected from halide, methanesulfonate and trifluoromethanesulfonate.

Furthermore, the compound of Formula (X) may be prepared by reacting a compound of Formula (XXII) with a compound R³—NH₂.

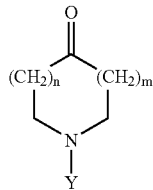

XXII

Certain intermediates described above are novel compounds and it is to be understood that all novel intermediates herein for further aspects of the present invention.

Racemic compounds may be separated either using preparative HPLC and a column with a chiral stationary phase, or resolved to yield individual enantiomers utilizing methods known to those skilled in the art. In addition, chiral intermediate compounds may be resolved and used to prepare chiral compounds of the invention.

According to a further aspect of the invention, there is provided one or more metabolites of the compounds of the invention when formed in vivo.

The compounds of the invention may have the advantage that they are more potent, have a longer duration of action, have a broader range of activity, are more stable, have fewer side effects or are more selective, or have other more useful properties than the compounds of the prior art.

The compounds of the invention are useful because they have pharmacological activity in mammals, including humans. Thus, they are useful in the treatment or prevention of disorders in which the regulation of monoamine transporter function is implicated, more particularly disorders in which inhibition of re-uptake of serotonin or noradrenaline is implicated, and especially those in which inhibition of serotonin and noradrenaline re-uptake is implicated.

Accordingly the compounds of the invention are useful in the treatment of urinary incontinence, such as genuine stress incontinence (GSI), urinary stress incontinence (USI) or urinary incontinence in the elderly; overactive bladder (OAB), including idiopathic detrusor instability, detrusor overactivity secondary to neurological diseases (e.g. Parkinson's disease, multiple sclerosis, spinal cord injury and stroke) and detrusor overactivity secondary to bladder outflow obstruction (e.g. benign prostatic hyperplasia (BPH), urethral stricture or stenosis); nocturnal eneuresis; urinary incontinence due to a combination of the above conditions (e.g. genuine stress incontinence associated with overactive bladder); and urinary symptoms, such as frequency and urgency.

In view of their aforementioned pharmacological activity the compounds of the invention are also useful in the treatment of depression, such as major depression, recurrent depression, single episode depression, subsyndromal symptomatic depression, depression in cancer patients, depression in Parkinson's patients, postmyocardial infarction depression, paediatric depression, child abuse induced depression, depression in infertile women, post partum depression, premenstrual dysphoria and grumpy old man syndrome.

In view of their aforementioned pharmacological activity the compounds of the invention are also useful in the treatment of cognitive disorders such as dementia, particularly degenerative dementia (including senile dementia, Alzheimer's disease, Pick's disease, Huntingdon's chorea, Parkinson's disease and Creutzfeldt-Jakob disease) and vascular dementia (including multi-infarct dementia), as well as dementia associated with intracranial space occupying lesions, trauma, infections and related conditions (including HIV infection), metabolism, toxins, anoxia and vitamin deficiency; mild cognitive impairment associated with ageing, particularly age associated memory impairment (AAMI), amnestic disorder and age-related cognitive decline (ARCD); psychotic disorders, such as schizophrenia and mania; anxiety disorders, such as generalised anxiety disorder, phobias (e.g. agoraphobia, social phobia and simple phobias), panic disorder, obsessive compulsive disorder, post traumatic stress disorder, mixed anxiety and depression; personality disorders such as avoidant personality disorder and attention deficit hyperactivity disorder (ADHD); sexual dysfunction, such as premature ejaculation, male erectile dysfunction (MED) and female sexual dysfunction (FSD) (e.g. female sexual arousal disorder (FSAD)); premenstrual syndrome; seasonal affective disorder (SAD); eating disorders, such as anorexia nervosa and bulimia nervosa; obesity; appetite suppression; chemical dependencies resulting from addiction to drugs or substances of abuse, such as addictions to nicotine, alcohol, cocaine, heroin, phenobarbital and benzodiazepines; withdrawal syndromes, such as those that may arise from the aforementioed chemical dependencies; cephalic pain, such as migraine, cluster headache, chronic paroxysmal hemicrania, headache associated with vascular disorders, headache associated with chemical dependencies or withdrawal syndromes resulting from chemical dependencies, and tension headache; pain; Parkinson's diseases, such as dementia in Parkinson's disease, neuroleptic-induced Parkinsonism and tardive dyskinesias); endocrine disorders, such as hyperprolactinaemia; vasospasm, such as in the cerebral vasculature; cerebellar ataxia; Tourette's syndrome; trichotillomania; kleptomania; emotional lability; pathological crying; sleeping disorder (cataplexy); and shock.

In view of their aforementioned pharmacological activity the compounds of the invention are also useful in the treatment of a number of other conditions or disorders, including hypotension; gastrointestinal tract disorders (involving changes in motility and secretion) such as irritable bowel syndrome (IBS), ileus (e.g. post-operative ileus and ileus during sepsis), gastroparesis (e.g. diabetic gastroparesis), peptic ulcer, gastroesophageal reflux disease (GORD, or its synonym GERD), flatulence and other functional bowel disorders, such as dyspepsia (e.g. non-ulcerative dyspepsia (NUD)) and non-cardiac chest pain (NCCP); and fibromyalgia syndrome.

In view of their aforementioned pharmacological activity, the compounds of the invention may also be useful in the treatment of pain. For example, pain from strains/sprains, post-operative pain (pain following any type of surgical procedure), posttraumatic pain, burns, myocardial infarction, acute pancreatitis, and renal colic. Also cancer related acute pain syndromes commonly due to therapeutic interactions such as chemotherapy toxicity, immunotherapy, hormonal therapy and radiotherapy. Further examples include tumour related pain, (e.g. bone pain, headache and facial pain, viscera pain) or associated with cancer therapy (e.g. postchemotherapy syndromes, chronic postsurgical pain syndromes, post radiation syndromes), back pain which may be due to herniated or ruptured intervertebral discs or abnormalities of the lumber facet joints, sacroiliac joints, paraspinal muscles or the posterior longitudinal ligament.

In addition, the compounds of the invention may be useful in the treatment of neuropathic pain. This is defined as pain initiated or caused by a primary lesion or dysfunction in the nervous system (IASP definition). Nerve damage can be caused by trauma and disease and thus the term 'neuropathic pain' encompasses many disorders with diverse aetiologies. These include but are not limited to, diabetic neuropathy, post herpetic neuralgia, back pain, cancer neuropathy, chemotherapy-induced neuropathy, HIV neuropathy, Phantom limb pain, Carpal Tunnel Syndrome, chronic alcoholism, hypothyroidism, trigeminal neuralgia, uremia, trauma-induced neuropathy, or vitamin deficiencies.

Other types of pain include but are not limited to:

Inflammatory pain, such as arthritic pain, including rheumatoid arthritis (RA) and ostoearthritis (OA), and inflammatory bowel disease (IBD);

Musculo-skeletal disorders including but not limited to myalgia, fibromyalgia, spondylitis, sero-negative (non-rheumatoid) arthropathies, non-articular rheumatism, dystrophinopathy, Glycogenolysis, polymyositis, pyomyositis;

Central pain or 'thalamic pain' as defined by pain caused by lesion or dysfunction of the nervous system including but not limited to central post-stroke pain, multiple sclerosis, spinal cord injury, Parkinson's disease and epilepsy;

Heart and vascular pain including but not limited to angina, myocardical infarction, mitral stenosis, pericarditis, Raynaud's phenomenon, scleradoma, skeletal muscle ischemia;

Visceral pain, and gastrointestinal disorders, including the pain associated with dysmenorrhea, pelvic pain, cystitis and pancreatitis;

Head pain including but not limited to migraine, migraine with aura, migraine without aura, cluster headache, tension-type headache; and Orofacial pain including but not limited to dental pain, temporomandibular myofascial pain.

Disorders of particular interest include urinary incontinence, such as mixed incontinence, GSI and USI; pain; depression; anxiety disorders, such as obsessive-compulsive disorder and post traumatic stress disorder; personality disorders, such as ADHD; sexual dysfunction; and chemical dependencies and withdrawal syndromes resulting from chemical dependencies.

Thus, according to further aspects, the invention provides:

i) a compound of the invention for use in human or veterinary medicine;

ii) a compound of the invention for use in the treatment of a disorder in which the regulation of monoamine transporter function is implicated, such as urinary incontinence;

iii) the use of a compound of the invention in the manufacture of a medicament for the treatment of a disorder in which the regulation of monoamine transporter function is implicated;

iv) a compound of the invention for use in the treatment of a disorder in which the regulation of serotonin or noradrenaline is implicated;

v) the use of a compound of the invention in the manufacture of a medicament for the treatment of a disorder in which the regulation of serotonin or noradrenaline is implicated;

vi) a compound of the invention for use in the treatment of a disorder in which the regulation of serotonin and noradrenaline is implicated;

vii) the use of a compound of the invention in the manufacture of a medicament for the treatment of a disorder in which the regulation of serotonin and noradrenaline is implicated;

viii) a compound of the invention for use in the treatment of urinary incontinence, such as GSI or USI;

ix) the use of a compound of the invention in the manufacture of a medicament for the treatment of urinary incontinence, such as GSI or USI;

x) a method of treatment of a disorder in which the regulation of monoamine transporter function is implicated which comprises administering a therapeutically effective amount of a compound of the invention to a patient in need of such treatment;

xi) a method of treatment of a disorder in which the regulation of serotonin or noradrenaline is implicated which comprises administering a therapeutically effective amount of a compound of the invention to a patient in need of such treatment;

xii) a method of treatment of a disorder in which the regulation of serotonin and noradrenaline is implicated which comprises administering a therapeutically effective amount of a compound of the invention to a patient in need of such treatment; and xiii) a method of treatment of urinary incontinence, such as GSI or USI, which comprises administering a therapeutically effective amount of a compound of the invention to a patient in need of such treatment.

It is to be appreciated that all references herein to treatment include curative, palliative and prophylactic treatment, unless explicitly stated otherwise.

The compounds of the invention may be administered alone or as part of a combination therapy. If a combination of therapeutic agents is administered, then the active ingredients may be administered either sequentially or simultaneously in separate or combined pharmaceutical formulations.

Examples of suitable agents for adjunctive therapy include:

an oestrogen agonist or selective oestrogen receptor modulator (e.g. HRT therapies or lasofoxifene);

an alpha-adrenergic receptor agonist, such as phenylpropanolamine or R-450;

an alpha-adrenergic receptor antagonist (e.g. phentolamine, doxazasin, tamsulosin, terazasin and prazasin), including a selective alpha$_{1L}$-adrenergic receptor antagonist (e.g. Example 19 of WO98/30560);

a beta-adrenergic agonist (e.g. clenbuterol);

a muscarinic receptor antagonist (e.g. tolterodine or oxybutinin), including a muscarinic M3 receptor antagonist (e.g. darifenacin);

a Cox inhibitor, such as a Cox-2 inhibitor (e.g. celecoxib, rofecoxib, valdecoxib parecoxib or etoricoxib);

a tachykinin receptor antagonist, such as a neurokinin antagonist (e.g. an NK1, NK2 or NK3 antagonist);

a beta 3 receptor agonist;

a 5HT$_1$ ligand (e.g buspirone);

a 5HT$_1$ agonist, such as a triptan (e.g. sumatriptan or naratriptan);

a dopamine receptor agonist (e.g. apomorphine, teachings on the use of which as a pharmaceutical may be found in U.S. Pat. No. 5,945,117), including a dopamine D2 receptor agonist (e.g. premiprixal, Pharmacia Upjohn compound number PNU95666; or ropinirole);

a melanocortin receptor agonist (e.g. melanotan II);

a PGE receptor antagonist;

a PGE1 agonist (e.g. alprostadil);

a further monoamine transport inhibitor, such as an noradrenaline re-uptake inhibitor (e.g. reboxetine), a serotonin re-uptake inhibitor (e.g. sertraline, fluoxtine, or paroxetine), or a dopamine re-uptake Inhibitors;

a 5-HT3 receptor antagonist (e.g. ondansetron, granisetron, tropisetron, azasetron, dolasetron or alosetron);

a phosphodiesterase (PDE) inhibitor, such as PDE2 inhibitor, (e.g. erythro-9-(2-hydroxyl-3-nonyl)-adenine or Example 100 of EP 0771799, incorporated herein by reference) and in particular a PDE5 inhibitor (e.g. sildenafil; 1-{[3-(3,4-dihydro-5-methyl-4-oxo-7-propylimidazo[5,1-f]-as-trazin-2-yl)-4-ethoxyphenyl]sulfonyl}-4-ethylpiperazine, i.e. vardenafil, also known as Bayer BA 38-9456; or Icos Lilly's IC351, see structure below).

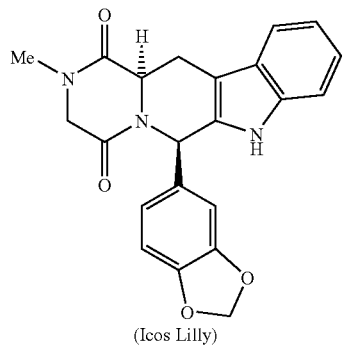
(Icos Lilly)

The invention thus provides, in a further aspect, a combination comprising a compound of the invention together with a further therapeutic agent.

For human use the compounds of the invention can be administered alone, but in human therapy will generally be administered in admixture with a suitable pharmaceutical excipient, diluent or carrier selected with regard to the intended route of administration and standard pharmaceutical practice.

For example, the compounds of the invention, can be administered orally, buccally or sublingually in the form of tablets, capsules (including soft gel capsules), ovules, elixirs, solutions or suspensions, which may contain flavouring or colouring agents, for immediate-, delayed-, modified-, sustained-, dual-, controlled-release or pulsatile delivery applications. The compounds of the invention may also be administered via intracavernosal injection. The compounds of the invention may also be administered via fast dispersing or fast dissolving dosage forms.

Such tablets may contain excipients such as microcrystalline cellulose, lactose, sodium citrate, calcium carbonate, dibasic calcium phosphate, glycine, and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention, and their pharmaceutically acceptable salts, may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients may be present both within the dosage form i.e. within the matrix, and/or on the dosage form, i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e. where the drug substance is insoluble a fast dispersing dosage form can be prepared and where the drug substance is soluble a fast dissolving dosage form can be prepared.

The compounds of the invention can also be administered parenterally, for example, intravenously, intra-arterially, intraperitoneally, intrathecally, intraventricularly, intraurethrally, intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

For oral and parenteral administration to human patients, the daily dosage level of the compounds of the invention or salts or solvates thereof will usually be from 10 to 500 mg (in single or divided doses).

Thus, for example, tablets or capsules of the compounds of the invention or salts or solvates thereof may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions (including PE), compounds of the invention may be taken as a single dose on an "as required" basis (i.e. as needed or desired).

Example Tablet Formulation

In general a tablet formulation could typically contain between about 0.01 mg and 500 mg of a compound according to the present invention (or a salt thereof) whilst tablet fill weights may range from 50 mg to 1000 mg. An example formulation for a 10 mg tablet is illustrated:

| Ingredient | % w/w |
| --- | --- |
| Free base or salt of compound | 10.000* |
| Lactose | 64.125 |
| Starch | 21.375 |
| Croscarmellose Sodium | 3.000 |
| Magnesium Stearate | 1.500 |

*This quantity is typically adjusted in accordance with drug activity and is based on the weight of the free base.

The compounds of the invention can also be administered intranasally or by inhalation and are conveniently delivered in the form of a dry powder inhaler or an aerosol spray presentation from a pressurised container, pump, spray or nebulizer with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg which may be administered in a single dose or, more usually, in divided doses throughout the day.

The compounds of the invention may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compounds of the invention can be administered in the form of a suppository or pessary, or they may be applied topically in the form of a gel, hydrogel, lotion, solution, cream, ointment or dusting powder. The compounds of the invention may also be dermally or transdermally administered, for example, by the use of a skin patch. They may also be administered by the ocular, pulmonary or rectal routes.

For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters, wax, cetearyl alcohol, 2-octyldodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

For oral or parenteral administration to human patients the daily dosage levels of compounds of formula (I), and their pharmaceutically acceptable salts, will be from 0.01 to 30 mg/kg (in single or divided doses) and preferably will be in the range 0.01 to 5 mg/kg. Thus tablets will contain 1 mg to 0.4 g of compound for administration singly or two or more at a time, as appropriate. The physician will in any event determine the actual dosage which will be most suitable for any particular patient and it will vary with the age, weight and response of the particular patient. The above dosages are, of course only exemplary of the average case and there may be instances where higher or lower doses are merited, and such are within the scope of the invention.

Oral administration is preferred.

For veterinary use, a compound of the invention is administered as a suitably acceptable formulation in accordance with normal veterinary practice and the veterinary surgeon will determine the dosing regimen and route of administration which will be most appropriate for a particular animal.

Thus according to a further aspect, the invention provides a pharmaceutical formulation containing a compound of the invention and a pharmaceutically acceptable adjuvant, diluent or carrier.

The combinations referred to above may also conveniently be presented for use in the form of a pharmaceutical formulation and thus pharmaceutical formulations comprising a combination as defined above together with a pharmaceutically acceptable adjuvant, diluent or carrier comprise a further aspect of the invention. The individual components of such combinations may be administered either sequentially or simultaneously in separate or combined pharmaceutical formulations.

When a compound of the invention is used in combination with a second therapeutic the dose of each compound may differ from that when the compound is used alone. Appropriate doses will be readily appreciated by those skilled in the art.

The invention is illustrated by the following non-limiting examples in which the following abbreviations and definitions may be used:

| | |
|---|---|
| APCI | Atmospheric pressure chemical ionisation |
| Arbacel ® | filter agent |
| br | Broad |
| BOC | tert-butoxycarbonyl |
| CDI | carbonyldiimidazole |
| δ | chemical shift |
| d | doublet |
| Δ | heat |
| DCCI | dicyclohexylcarbodiimide |
| DCM | dichloromethane |
| DMF | N,N-dimethylformamide |
| DMSO | dimethylsulfoxide |
| ES+ | electrospray ionisation positive scan |
| ES− | electrospray ionisation negative scan |
| h | hours |
| HOAT | 1-hydroxy-7-azabenzotriazole |
| HOBT | 1-hydroxybenzotriazole |
| HPLC | high pressure liquid chromatography |
| m/z | mass spectrum peak |
| min | minutes |
| MS | mass spectrum |
| NMM | N-methyl morpholine |
| NMR | nuclear magnetic resonance |
| q | quartet |
| s | singlet |
| t | triplet |
| TBTU | 2-(1H-benzotriazol-1-yl)-1,1,3,3-tetramethyluronium tetrafluoroborate |
| Tf | trifluoromethanesulfonyl |
| TFA | trifluoroacetic acid |
| THF | tetrahydrofuran |
| TLC | thin layer chromatography |
| TS+ | thermospray ionisation positive scan |
| WSCDI | 1-(3-dimethylaminopropyl)-3-ethylcarbodiimide hydrochloride |

The Preparations and Examples that follow illustrate the invention but do not limit the invention in any way. All temperatures are in ° C. Flash column chromatography was carried out using Merck silica gel 60 (9385). Solid Phase Extraction (SPE) chromatography was carried out using Varian Mega Bond Elut (Si) cartridges (Anachem) under 15 mmHg vacuum. Thin layer chromatography (TLC) was carried out on Merck silica gel 60 plates (5729). Melting points were determined using a Gallenkamp MPD350 apparatus and are uncorrected. NMR was carried out using a Varian-Unity Inova 400 MHz nmr spectrometer or a Varian Mercury 400 MHz nmr spectrometer. Mass spectroscopy was carried out using a Finnigan Navigator single quadrupole electrospray mass spectrometer or a Finnigan aQa APCI mass spectrometer.

Preparation 1 tert-Butyl (3R)-1-(trifluoroacetyl)pyrrolidin-3-ylcarbamate

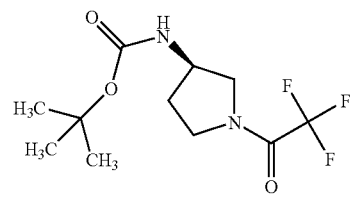

(3R)-3-(tert-Butoxycarbonylamino)pyrrolidine (3.0 g, 16.1 mmol—commercially available from Flurochem) and pyridine (3.87 mL, 48.3 mmol) were dissolved in dichloromethane (55 mL) and the reaction mixture stirred under nitrogen at 0° C. for 1 hour. A solution of trifluoroacetic acid anhydride (2.74 mL, 32.2 mmol) in dichloromethane (5 mL) was added dropwise to the reaction mixture over 10 minutes. The reaction mixture was allowed to warm to room temperature and stirred for 2 hours. The reaction mixture was diluted with dichloromethane (100 mL) and washed with saturated sodium hydrogencarbonate solution, water and then brine. The organic layer was separated, dried over magnesium sulphate and concentrated in vacuo. The crude product was azeotroped with toluene (2×30 mL) to yield the title product.

$^1$HNMR(DMSO-$D_6$, 400 MHz): 1.40 (s, 9H), 1.82 (dd, 1H), 2.08 (dd, 1H), 3.33(m, 1H), 3.46(m, 1H), 3.59-3.77 (brm, 2H), 4.06 (m, 1H), 7.22 (m, 1H) MS ES+m/z 281 [MH]+

Preparation 2

(3R)-1-(Trifluoroacetyl)pyrrolidin-3-amine hydrochloride

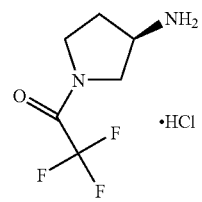

The Boc protected amine of preparation 1 (4.59 g, 16.1 mmol) was dissolved in dichloromethane (100 mL) and the reaction mixture stirred at 0° C. for 1 hour. Hydrogen chloride gas was then bubbled through the solution for 10 minutes and the reaction mixture allowed to warm to room temperature. Hydrogen chloride gas and nitrogen gas were then bubbled through the solution for 15 and 10 minutes respectively and the reaction mixture concentrated in vacuo to yield the title product.

$^1$HNMR(CDCl$_3$, 400 MHz): 1.27 (m, 2H), 1.65 (m, 1H), 1.81 (m, 1H), 2.10 (m, 2H), 3.32 (m, 2H), 3.61 (m, 1H) MS ES+m/z 183 [MH]+

Preparation 3 tert-Butyl (3S)-3-(isobutylamino)pyrrolidine-1-carboxylate

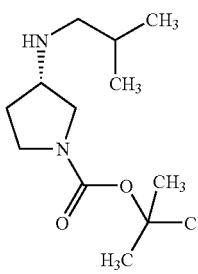

(3S) 3-Amino-pyrrolidine-1-carboxylic acid tert-butyl ester (3 g, 16.1 mmol) was added to a solution of isobutyraldehyde (1.61 mL, 17.7 mmol) and 10% Pd/C (360 mg) in ethanol (60 mL) and the reaction mixture left under about 415 kPa (about 60 psi) of hydrogen gas for 18 hours. The reaction mixture was filtered through Arbocel®, washing through thoroughly with ethyl acetate. The filtrate was concentrated in vacuo and the crude product purified by column chromatography on silica gel eluting with ethyl acetate:pentane 1:1 to yield the title product, 2.8 g, (73%).

$^1$HNMR (CDCl$_3$, 400 MHz): 0.92 (d, 6H), 1.44 (s, 9H), 1.63 (m, 2H), 2.00 (m, 1H), 2.39 (m, 2H), 3.02 (m, 1H), 3.25 (m, 2H), 3.48 (m, 2H), 3.60 (m, 1H) MS APCI+243 [MH$^+$]

Preparation 4

(3S)-N-Butyl-1-(trifluoroacetyl)pyrrolidin-3-amine

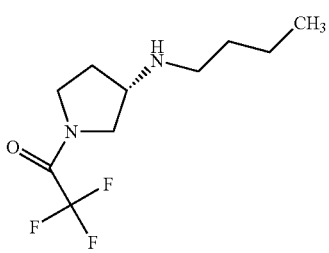

Triethylamine (1.9 mL, 13.72 mmol) and butanal (1.3 mL, 14.41 mmol) were added to a solution of (S)-1-(trifluoroacetyl)pyrrolidin-3-yl amine (3.0 g, 13.72 mmol) (J. Med. Chem., 1996, 39(14), pg. 2771, No. 6) in ethanol (60 mL). The reaction mixture was treated with 10% Pd/C (300 mg) and placed under about 415 kPa (about 60 psi) of hydrogen at room temperature for 18 hours. The reaction mixture was filtered through Arbocel®, washing through with ethyl acetate. The filtrate was washed with saturated sodium hydrogencarbonate solution, dried over magnesium sulphate and concentrated in vacuo. The crude product was purified by column chromatography on silica gel eluting with ethyl acetate:pentane:triethylamine 25:75:0 to 100:0:0 to 99:0:1 to yield the title product.

$^1$HNMR(CDCl$_3$, 400 MHz): 1.01 (t, 3H), 1.38 (m, 2H), 1.47 (m, 2H), 1.86-2.09 (m, 2H), 2.62 (m, 2H), 3.38-3.87 (brm, 6H) MS APCI+m/z 239 [MH]$^+$

Preparation 5

(3S)-N-Isobutyl-1-(trifluoroacetyl)pyrrolidin-3-amine

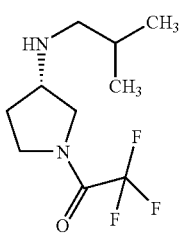

This compound was prepared by a method similar to that described for preparation 4 using isobutyralydehyde.

$^1$HNMR(CDCl$_3$, 400 MHz): 0.91 (t, 6H), 1.26 (d, 2H), 1.47 (m, 2H), 1.72 (m, 1H), 2.42 (m, 2H), 3.39 (m, 2H), 3.77 (m, 1H), 4.09 (m, 1H) MS APCI+m/z 239 [MH]$^+$

Preparation 6

(3S)-1-Benzyl-N-(2-naphthylmethyl)pyrrolidin-3-amine

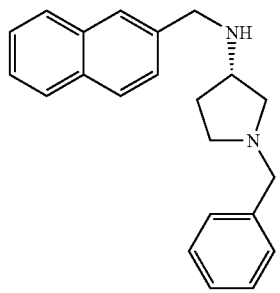

A solution of 2-naphthaldehyde (2.0 g, 12.8 mmol) and (3S)-1-benzyl-3-amino-pyrrolidine (2.37 g, 13.4 mmol) in methanol (30 mL) was stirred under nitrogen at room temperature for 6 hours. Sodium borohydride (969 mg, 25.6 mmol) was added and the reaction mixture left at room temperature for 18 hours. The reaction mixture was diluted with water and extracted into ethyl acetate (×3) and the organics were combined, dried over magnesium sulphate, and concentrated in vacuo. The crude product was purified by column chromatography on silica gel eluting with dichloromethane:methanol 100:0 to 97:3 to yield the title product, 4.01 g.

$^1$HNMR(CDCl$_3$, 400 MHz): 1.62 (m, 1H), 2.19 (m, 1H), 2.48 (m, 2H), 2.80 (m, 2H), 3.42 (m, 1H), 3.63 (s, 2H), 3.92 (m, 2H), 7.26 (m, 5H), 7.44 (m, 3H), 7.78 (m, 4H) MS APCI+m/z 317 [MH]$^+$

Preparation 7

(3R)-1-Benzyl-N-(2-naphthylmethyl)pyrrolidin-3-amine

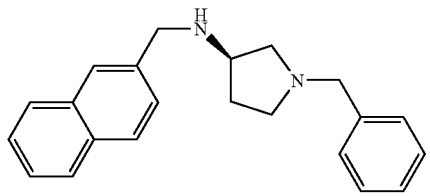

The title compound was prepared by a method similar to that described for preparation 6 using (3R)-1-benzyl-3-amino-pyrrolidine.

$^1$HNMR(CDCl$_3$, 400 MHz): 1.65 (m, 1H), 2.18 (m, 1H), 2.51 (m, 2H), 2.78 (m, 2H), 3.41 (m, 1H), 3.63 (m, 2H), 3.94 (s, 2H), 7.22 (m, 1H), 7.28 (m, 4H), 7.43 (m, 3H), 7.79 (m, 4H) MS APCI+m/z 317 [MH]$^+$

Preparation 8

(3R)-N-(3,4-Dichlorobenzyl)-1-(trifluoroacetyl)pyrrolidin-3-amine

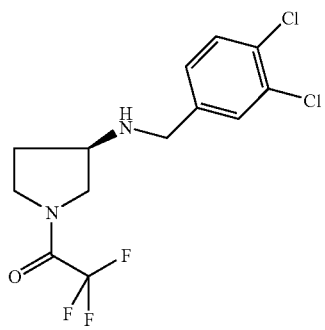

This compound was prepared by a method similar to that described in preparation 6 using the amine of preparation 2 and 3,4-dichlorobenzaldehyde.

$^1$HNMR(DMSO-D$_6$, 400 MHz): 1.88 (m, 2H), 2.63 (m, 1H), 3.36-3.78 (m, 7H), 7.32 (m, 1H), 7.59 (m, 2H) MS APCI+m/z 341 [MH]$^+$

Preparation 9

(3R)-N-(2,3-Dichlorobenzyl)-1-(trifluoroacetyl)pyrrolidin-3-amine

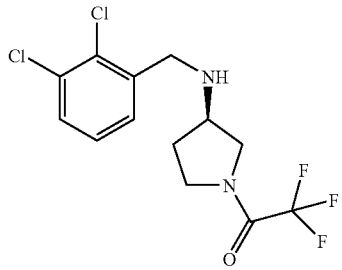

This compound was prepared by a method similar to that described for preparation 6 using the amine of preparation 2 and 2,3-dichlorobenzaldehyde.

$^1$HNMR(DMSO-D$_6$, 400 MHz): 1.92 (m, 2H), 3.29-3.74 (m, 7H), 3.83 (m, 1H), 7.27 (m, 1H), 7.51 (m, 2H) MS APCI+m/z 341 [MH]$^+$

Preparations 10-12

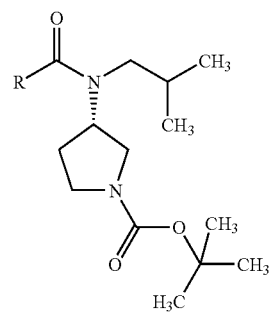

The appropriate carboxylic acid, RCO$_2$H (1 mmol), was dissolved in dichloromethane (5 mL), cooled in an ice bath, and the cooled solution treated with oxalyl chloride (0.248 mL, 2.5 mmol) and 1 drop of N,N-dimethylformamide. The ice was removed and the reaction mixture allowed to warm to room temperature and was then stirred at room temperature for 2 hours. The reaction mixture was concentrated in vacuo and the product added to a solution of triethylamine (0.229 mL, 1.64 mmol) and the amine of preparation 3 (200 mg, 0.83 mmol) in dioxane (10 mL). The reaction mixture was heated to 70° C. for 45 minutes and then allowed to cool to room temperature. The reaction mixture was concentrated in vacuo and the product taken up in dichloromethane and washed with 10% citric acid solution and 2M sodium hydroxide solution. The organic layer was separated and concentrated in vacuo. The crude product was purified by column chromatography on silica gel eluting with dichloromethane:methanol 100:0 to 98:2 to yield the title products.

| Prep. No. | R | Data |
|---|---|---|
| 10 | 2-Cl, 6-CH$_3$ phenyl | MS APCI+ m/z 295 [MH]$^+$ |
| 11 | 2-F, 6-CH$_3$ phenyl | $^1$HNMR (CDCl$_3$, 400 MHz): Mixture of rotamers 0.78, 0.98 (2xbs, 6H), 1.42, 1.44 (2xs, 9H), 1.58-2.50 (m, 6H), 2.88-4.78 (m, 6H), 4.08, 4.38 (2xm, 1H), 6.96 (m, 1H), 7.03 (m, 1H), 7.20 (m, 1H) MS APCI+ m/z 279 [MH]$^+$ |
| 12 | 2-OCH$_3$, 6-CH$_3$ phenyl | MS APCI+ m/z 291 [MH]$^+$ |

Preparation 13 tert-Butyl (3S)-3-[(2.3-dichlorobenzoyl)(isobutyl)amino]pyrrolidine-1-carboxylate

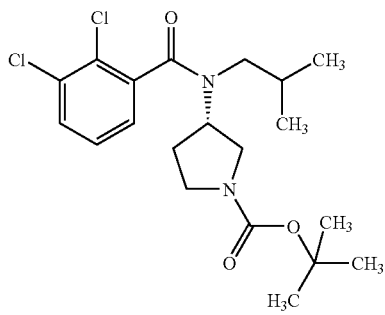

The amine of preparation 3 (200 mg, 0.826 mmol) was added to a solution of triethylamine (0.229 mL, 1.652 mmol) in dioxan (5 mL) and the reaction mixture treated with 2,3-dichloro-benzoyl chloride (207 mg, 0.99 mmol). The reaction mixture was heated to 70° C. and stirred for 90 minutes. The reaction mixture was concentrated in vacuo and the product taken up in dichloromethane and washed with 2M sodium hydroxide and 10% citric acid solution. The organics were separated and concentrated in vacuo. The crude product was purified by column chromatography on silica gel eluting with dichloromethane to yield the title product, 278 mg, (81%).

MS APCI+m/z 315 [MH]$^+$

Preparations 14-17

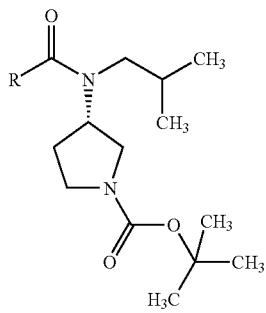

The following compounds of the general formula above were prepared by a method similar to that described in preparation 13 using the amine from preparation 3 and the appropriate acid chloride:

| Prep. No. | R | Data |
|---|---|---|
| 14 | 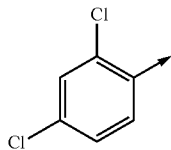 | MS APCI+ m/z 315 [MH]$^+$ |
| 15 | Cl-phenyl (3-Cl) | $^1$HNMR (CDCl$_3$, 400 MHz): poor resolution: 0.78 (bs, 6H), 1.37 (s, 9H), 2.00 (bm, 3H), 2.41 (s, 1H), 3.04 (bm, 3H), 3.43 (bm, 2H), 4.19 (bm, 1H), 7.14 (d, 1H), 7.23 (m, 3H) MS APCI+ m/z 281 [MH]$^+$ |
| 16 | Cl-phenyl (4-Cl) | $^1$HNMR (CDCl$_3$, 400 MHz): poor resolution: 0.78 (bs, 6H), 1.36 (s, 9H), 1.93 (bm, 2H), 2.05 (bm, 1H), 2.48 (s, 1H), 3.04 (bm, 3H), 3.43 (bm, 2H), 4.20 (bm, 1H), 7.21 (d, 2H), 7.28 (d, 2H) MS APCI+ m/z 281 [MH]$^+$ |
| 17 | Cl,Cl-phenyl (3,4-diCl) | $^1$HNMR (CDCl$_3$, 400 MHz): poor resolution: MS APCI+ m/z 315 [MH]$^+$ |

Preparation 18

N-[(3S)-1-Benzylpyrrolidin-3-yl]-N-(2-naphthylmethyl)benzamide

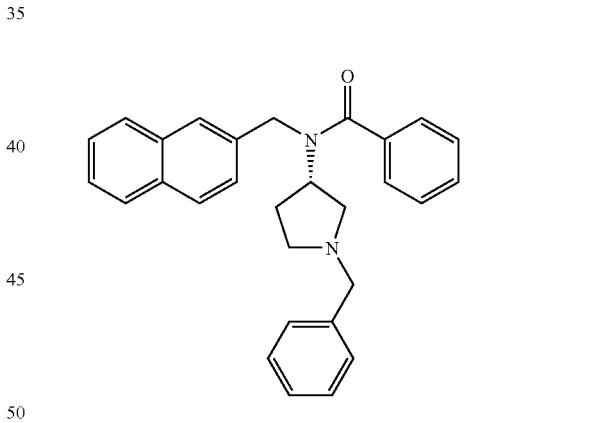

Benzoyl chloride (0.12 mL, 1.043 mmol) was added to a solution of the amine of preparation 6 (300 mg, 0.948 mmol) and triethylamine (0.26 μL, 1.896 mmol) in dichloromethane (5 mL) and the reaction mixture left under nitrogen at room temperature for 18 hours. The reaction mixture was washed with water and then with brine, dried over magnesium sulphate and concentrated in vacuo to yield the title product, 380 mg.

$^1$HNMR(CDCl$_3$, 400 MHz): 1.83-2.62 (brm, 4H), 2.84 (m, 2H), 3.62 (m, 2H) 4.56 (m, 1H), 5.05 (m, 2H), 7.24 (m, 4H), 7.31-7.60 (m, 9H), 7.78 (m, 4H) MS ES+m/z 421 [MH]$^+$

Preparation 19

N-[(3R)-1-Benzylpyrrolidin-3-yl]-N-(2-naphthylmethyl)benzamide

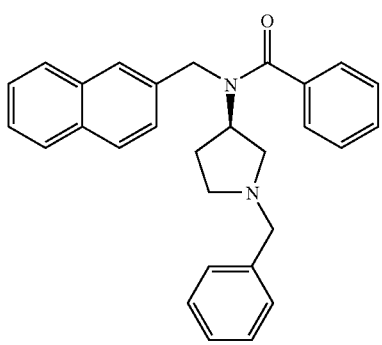

The title compound was prepared using a method similar to that described for preparation 18 using the amine of preparation 7.

$^1$HNMR(CDCl$_3$, 400 MHz): 1.94-2.58 (brm, 6H), 2.86 (m, 2H), 3.62 (m, 1H), 5.08 (m, 2H), 7.23 (m, 4H), 7.34-7.60 (m, 9H), 7.79 (m, 4H) MS APCI+m/z 421 [MH]$^+$

Preparation 20

N-Butyl-N-[(3S)-1-(trifluoroacetyl)pyrrolidin-3-yl]-1-naphthamide

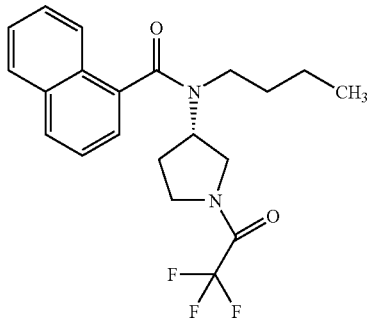

This compound was prepared by a method similar to that described for preparation 18 using the amine of preparation 4 and 1-naphthoyl chloride.

$^1$HNMR(CDCl$_3$, 400 MHz): 0.61 (m, 2H), 0.98 (m, 3H), 1.32-1.60 (brm, 4H), 3.06 (m, 2H), 3.27-3.76 (m, 4H), 5.28 (m, 1H), 7.39 (m, 1H), 7.45 (m, 3H), 7.72 (m, 1H), 7.89 (m, 2H) MS APCI+m/z 393 [MH]$^+$

Preparation 21

N-Isobutyl-N-[(3S)-1-(trifluoroacetyl)pyrrolidin-3-yl]-2-naphthamide

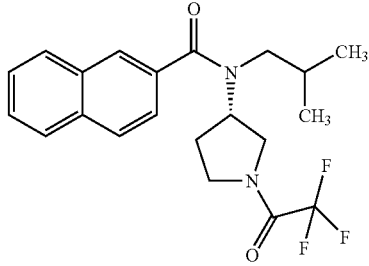

This compound was prepared by a method similar to that described for preparation 18 using 1-napthoyl chloride and the amine of preparation 3.

$^1$HNMR(CDCl$_3$, 400 MHz): 0.84 (m, 8H), 2.00 (m, 1H), 3.25 (m, 2H), 3.93 (m, 2H), 4.38 (brm, 1H), 5.31 (m, 2H), 7.24 (m, 2H), 7.38-7.62 (m, 5H) MS APCI+m/z 393 [MH]$^+$

Preparation 22

4-Chloro-N-(3,4-dichlorobenzyl)-N-[(3R)-1-(trifluoroacetyl)pyrrolidin-3-yl]benzamide

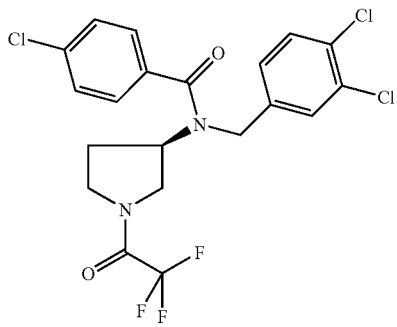

The amine of preparation 8 (180 mg, 0.58 mmol) was dissolved in dichloromethane (3 mL) and the reaction mixture treated with triethylamine (0.16 mL, 1.16 mmol). The reaction mixture was cooled to 0° C. and 4-chlorobenzoyl chloride (0.08 mL, 0.63 mmol) added dropwise. The reaction mixture was stirred under nitrogen for 18 hours. The reaction mixture was diluted with further dichloromethane and washed with water. The organic layer was dried over magnesium sulphate and concentrated in vacuo. The crude product was purified by column chromatography on silica gel eluting with dichloromethane:methanol 100:0 to 95:5 to yield the title product.

$^1$HNMR(DMSO-D$_6$, 400 MHz): 2.02 (m, 2H), 3.37-3.72 (m, 4H), 4.61 (m, 2H), 5.68 (m, 1H), 7.22-7.59 (m, 7H) MS APCI+m/z 479 [MH]$^+$

Preparation 23

4-Chloro-N-(2,3-dichlorobenzyl)-N-[(3R)-1-(trifluoroacetyl)pyrrolidin-3-yl]benzamide

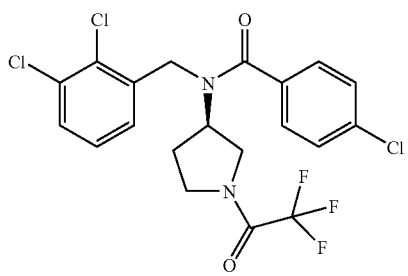

This compound was prepared by a method similar to that described for preparation 22 using the amine of preparation 9.

$^1$HNMR(DMSO-D$_6$, 400 MHz): 2.04 (m, 2H), 3.37-3.76 (m, 4H), 4.46-4.76 (m, 3H), 7.22-7.58 (brm, 7H) MS APCI+ m/z 479 [MH]$^+$

EXAMPLE 1

2,3-Dichloro-N-isobutyl-N-[(3S)-pyrrolidin-3-yl]benzamide citrate

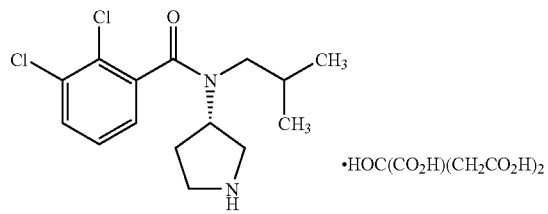

The Boc protected product of preparation 13 (10.55 g, 25.4 mmol) was dissolved in dichloromethane (20 mL) under nitrogen and the reaction mixture treated with trifluoroacetic acid (20 mL, 260.5 mmol). The reaction mixture was then stirred at room temperature for 4.5 hours. The reaction mixture was concentrated in vacuo and the residue taken up in dichloromethane (200 mL) and washed with 1M sodium hydroxide solution (100 mL). The organic phase was separated, dried over magnesium sulphate and concentrated in vacuo. The residue was azeotroped with ethyl acetate (10×) and then dried under vacuum to yield the free base of the title product as a colourless oil, 7.281 g (91%). A portion of this product (3.327 g, 10.56 mmol) was treated with a solution of citric acid (2.028 g, 10.56 mmol) in methanol, concentrated in vacuo and dried under high vacuum to yield the title product as a pink solid, 4.71 g.

$^1$HNMR (MeOD, 400 MHz): 0.80 (t, 6H), 1.89 (m, 2H), 2.11 (brm, 2H), 2.53 (m, 2H), 2.68-2.91 (m, 4H), 3.59 (m, 1H), 3.82 (m, 2H), 4.37 (m, 1H), 7.40 (m, 2H), 7.61 (m, 1H) MS APCI+m/z 315 [MH$^+$]

EXAMPLE 2

2,4-Dichloro-N-isobutyl-N-[(3S)-pyrrolidin-3-yl]benzamide hydrochloride

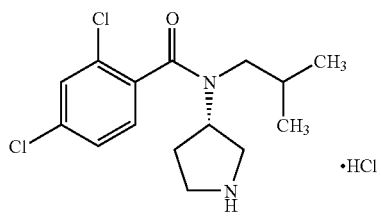

The BOC protected product of preparation 14 (157 mg, 0.561 mmol) was added to a solution of 4M hydrochloric acid in dioxan (1 mL) in dichloromethane (5 mL) and the reaction mixture stirred at room temperature for 18 hours. The reaction mixture was concentrated in vacuo and the product azeotroped with dichloromethane and ether and then triturated with ether to yield the title product, 103.3 mg, (87%).

$^1$HNMR (MeOD, 400 MHz): 0.80 (m, 6H), 1.89 (m, 1H), 2.51 (m, 2H), 2.90 (m, 1H), 3.20 (m, 2H), 3.52 (m, 1H), 3.78 (m, 2H), 4.30 (m, 1H), 7.40 (m, 1H), 7.46 (d, 1H), 7.58 (s, 1H) MS APCI+m/z 315 [MH$^+$]

EXAMPLES 3-8

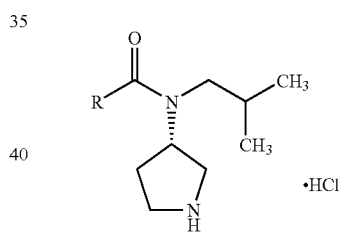

The following compounds of the general formula above were prepared by a method similar to that described in example 2 to give the hydrochloride salt of the compounds shown:

| Ex. No. | R | Data |
|---|---|---|
| 3 | ![2-chloro-3-methylphenyl] | $^1$HNMR (MeOD, 400 MHz): 0.80 (m, 6H), 1.91 (m, 1H), 2.41 (s, 3H), 2.54 (m, 2H), 2.88 (m, 1H), 3.20 (m, 2H), 3.53 (m, 1H), 3.79 (m, 2H), 4.34 (m, 1H), 7.20 (q, 1H), 7.32 (t, 1H), 7.41 (d, 1H) MS APCI+ m/z 295 [MH$^+$] |
| 4 | ![2-fluoro-3-methylphenyl] | $^1$HNMR (MeOD, 400 MHz): 0.80 (d, 6H), 1.90 (m, 1H), 2.20 (s, 3H), 2.53 (m, 2H), 2.97 (m, 1H), 3.20 (m, 3H), 3.54 (t, 1H), 3.79 (m, 1H), 4.32 (m, 1H), 7.06 (bs, 1H), 7.16 (t, 1H), 7.30 (q, 1H) MS APCI+ m/z 279 [MH$^+$] |

| Ex. No. | R | Data |
|---|---|---|
| 5 | 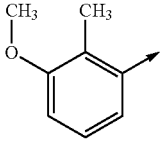 | ¹HNMR (MeOD, 400 MHz): 0.88 (d, 6H), 1.88 (m, 1H), 2.12 (d, 3H), 2.53 (m, 2H), 2.98 (m, 1H), 3.16 (m, 1H), 3.22 (m, 1H), 3.52 (m, 1H), 3.78 (m, 2H), 3.86 (s, 3H), 4.30 (m, 1H), 6.80 (q, 1H), 7.00 (d, 1H), 7.23 (t, 1H) MS APCI+ m/z 291 [MH⁺] |
| 6 | 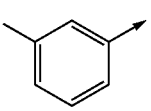 | ¹HNMR (MeOD, 400 MHz): 0.83 (d, 6H), 1.91 (m, 1H), 2.52 (m, 2H), 3.15 (d, 2H), 3.22 (m, 1H), 3.55 (t, 1H), 3.75 (m, 2H), 4.32 (m, 1H), 7.38 (d, 1H), 7.50 (m, 3H) MS ES+ m/z 281 [MH]⁺ |
| 7 | 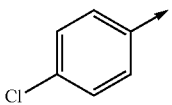 | ¹HNMR (MeOD, 400 MHz): 0.82 (d, 6H), 1.92 (m, 1H), 2.53 (m, 2H), 3.20 (d, 2H), 3.25 (m, 1H), 3.54 (t, 1H), 3.76 (m, 2H), 4.30 (m, 1H), 7.25 (dd, 4H) MS ES+ m/z 281 [MH]⁺ |
| 8 | 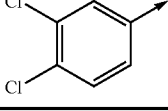 | ¹HNMR (MeOD, 400 MHz): 0.82 (d, 6H), 1.91 (m, 1H), 2.51 (m, 2H), 3.19 (m, 3H), 3.51 (t, 1H), 3.72 (m, 2H), 4.31 (m, 1H), 7.35 (d, 1H), 7.65 (m, 2H) MS ES+ m/z 315 [MH]⁺ |

EXAMPLE 9
N-(2-Naphthylmethyl)-N-[(3S)-pyrrolidin-3-yl]benzamide hydrochloride

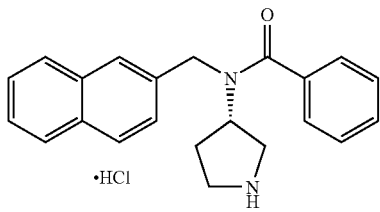

A solution of the benzyl protected product of preparation 18 (370 mg, 88 mmol), ammonium formate (555 mg, 8,798 mmol) and 10% Pd/C (40 mg) in ethanol (5 mL) was refluxed under nitrogen for 6 hours. The reaction mixture was filtered through Arbocel®, washing through with ethanol, and the filtrate concentrated in vacuo. The crude product was purified by column chromatography on silica gel eluting with dichloromethane:methanol:0.88 ammonia 100:0:0 to 90:10:1. The product was dissolved in the minimum of a solution of etherial hydrochloric acid in dichloromethane and concentrated in vacuo. The product was triturated with ether (×3) and dried under vacuum to yield the title product, 120 mg, (36%).

¹HNMR(DMSO-D₆, 400 MHz): 2.06 (m, 2H), 2.98 (brs, 1H), 3.79 (m, 3H), 4.43 (m, 1H), 4.71 (m, 2H), 7.25-7.59 (m, 9H), 7.78 (m, 1H), 7.93 (m, 3H) MS APCI+m/z 331 [MH]⁺

EXAMPLE 10
N-(2-Naphthylmethyl)-N-[(3R)-pyrrolidin-3-yl]benzamide hydrochloride

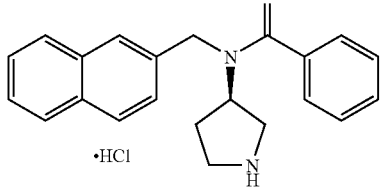

The title compound was prepared using a method similar to that described for example 9, using the benzyl protected product of preparation 19 as a starting material. 160 mg, (47%), of the title product was collected.

¹HNMR(DMSO-D₆, 400 MHz): 2.11 (m, 2H), 3.00 (m, 1H), 3.35 (brm, 3H), 4.44 (m, 1H), 4.78 (m, 2H), 7.28-7.56 (brm, 9H), 7.81 (m, 1H), 7.96 (m, 3H) MS ES+m/z 331 [MH]⁺

EXAMPLE 11
N-Isobutyl-N-[(3S)-pyrrolidin-3-yl]-2-naphthamide hydrochloride

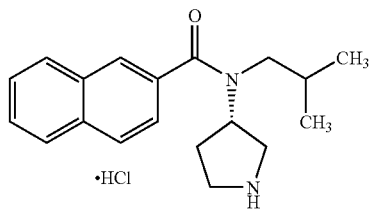

Potassium carbonate (92 mg, 0.66 mmol) was added to a solution of the trifluoroacetate protected product of preparation 21 (130 mg, 0.33 mmol) in water (0.5 mL) and methanol (5 mL) and the reaction mixture stirred at room temperature for 18 hours. The reaction mixture was concentrated in vacuo and the crude product dissolved in a mixture of 10% potassium carbonate solution:ethyl acetate 1:1 (25 mL). The organic phase was dried over magnesium sulphate and concentrated in vacuo. The crude product was dissolved in ethyl acetate, treated with 1M hydrochloric acid in ether and stirred at room temperature for 1 hour. The reaction mixture was concentrated in vacuo to yield the title product.

¹HNMR(MeOD, 400 MHz): 0.79 (d, 6H), 1.93 (m, 1H), 2.56 (m, 2H), 3.25 (m, 3H), 3.55 (t, 1H), 3.80 (m, 2H), 4.36 (m, 1H), 7.48 (d, 1H), 7.59 (m, 2H), 7.96 (m, 4H) MS ES+m/z 298 [MH⁺]

EXAMPLE 12
N-Butyl-N-[(3S)-pyrrolidin-3-yl]-1-naphthamide hydrochloride

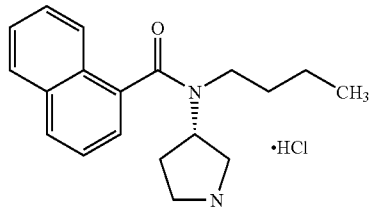

This compound was prepared by a method similar to that described for example 11 using the trifluoroacetate protected product of preparation 20 as a starting material.

¹HNMR(MeOD, 400 MHz): 0.62 (m, 3H), 1.04 (m, 2H), 1.72 (m, 2H), 2.65 (m, 2H), 3.07 (m, 2H), 3.21 (m, 1H), 3.59 (m, 1H), 3.87 (m, 2H), 4.42 (m, 1H), 7.30 (s, m, 1H), 7.57 (m, 3H), 7.78 (m, 1H), 8.00 (m, 2H) MS ES+m/z 297 [MH]⁺

EXAMPLE 13

4-Chloro-N-(3,4-dichlorobenzyl)-N-[(3R)-pyrrolidin-3-yl]benzamide hydrochloride

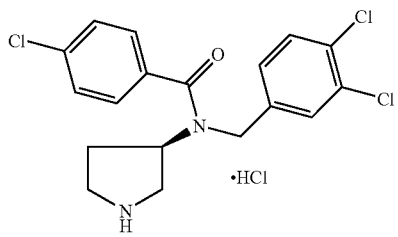

This compound was prepared by a method similar to that described for example 11 using trifluoroacetate protected product of preparation 22 as a starting material. 75 mg, (47%), of the title product was collected.

¹HNMR(DMSO-D₆, 400 MHz): 1.58 (m, 1H), 1.83 (m, 1H), 2.60 (m, 1H), 2.81 (m, 2H), 3.42 (m, 2H), 4.61 (m, 2H), 7.25 (m, 1H), 7.39-7.59 (m, 7H)

EXAMPLE 14

4-Chloro-N-(2,3-dichlorobenzyl)-N-[(3R)-pyrrolidin-3-yl]benzamide hydrochloride

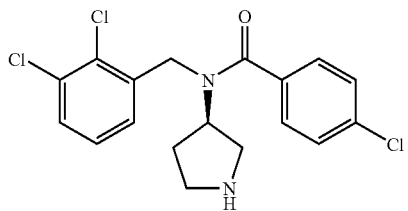

This compound was prepared by a method similar to that described for example 11 using the trifluoroacetate protected product of preparation 23 as a starting material. 90 mg, (52%), of the title product was collected.

¹HNMR(DMSO-D₆, 400 MHz): 1.62 (m, 1H), 1.88 (m, 1H), 2.61 (m, 2H), 2.85 (m, 2H), 4.28 (m, 1H), 4.59 (t, 2H), 7.24 (m, 1H), 7.36 (m, 1H), 7.42-7.58 (m, 6H) MS ES+m/z 385 [MH]⁺

EXAMPLE 15

2,4-Dichloro-5-fluoro-N-isobutyl-N-[(3S)-pyrrolidin-3-yl]benzamide hydrochloride

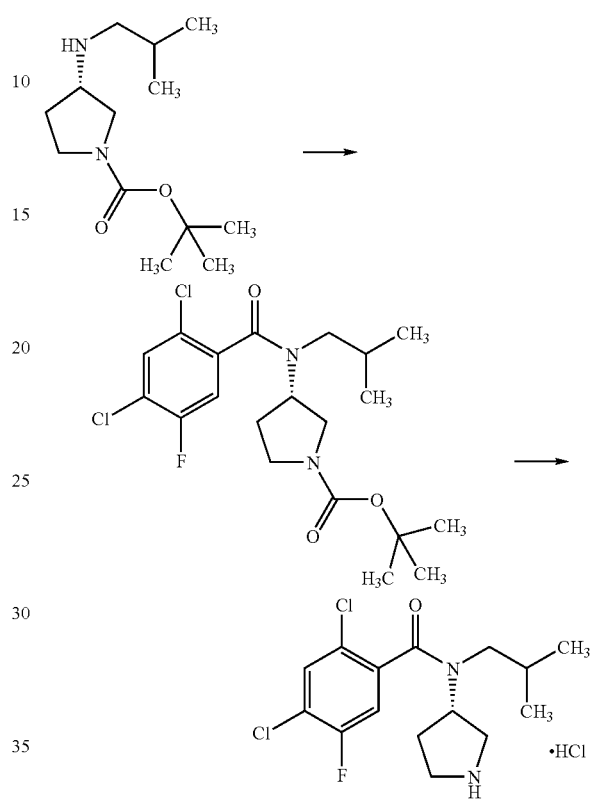

tert-Butyl (3S)-3-[(2,4-dichloro-5-fluorobenzoyl)(isobutyl)amino]pyrrolidine-1-carboxylate was prepared by a method similar to that described in preparation 13 using the amine of preparation 3 and 2,4-dichloro-5-fluorobenzoyl chloride to yield the desired product, 340 mg.

MS ES+m/z 455 [MNa]⁺.

2,4-Dichloro-5-fluoro-N-isobutyl-N-[(3S)-pyrrolidin-3-yl]benzamide hydrochloride was prepared from the foregoing compound by a method similar to that described in example 2 to yield the title product as an off-white solid, 100 mg.

MS APCI+m/z 333 [MH]⁺. Found: C, 47.22; H, 5.87; N, 7.08%. Calc. for C₁₅H₁₉Cl₂FN₂O.HCl.0.7H₂O: C, 47.17; H, 5.64; N, 7.33%.

EXAMPLE 16

The NRI IC₅₀ and the SRI IC₅₀ of the compounds of Examples 1 to 14 were determined as follows. The results are set out below in Table 1.

Biological Activity

The compounds were tested for biological activity by their ability to inhibit the uptake of serotonin and/or noradrenaline by human serotonin and/or noradrenaline transporters as follows.

(i) Cell Culture

Human embryonic kidney cells (HEK-293) stably transfected with either the human serotonin transporter (hSERT), noradrenaline transporter (hNET) or dopamine transporter (hDAT) were cultured under standard cell culture techniques (cells were grown at 37° C. and 5% $CO_2$ in either Dulbecco's Modified Eagle's Medium (DMEM) culture media supplemented with 10% dialysed foetal calf serum (FCS), 2 mM L-glutamine and 250 μg/ml geneticin (hSERT and hNET cells) or DMEM-culture media supplemented with 5% FCS, 5% new-born calf serum, 2 mM L-glutamine and 2.5 mg/ml puromycin (hDAT cells)). Prior to assay, cells were harvested by dissociation using cell dissociation solution (Sigma) and centrifugation, and resuspended in standard assay buffer (see below) at a viable cell density of 750,000 cells/ml.

(i) Determination of Inhibitor Potency

All test compounds were dissolved in 100% DMSO at 4 mM and diluted down in 1% DMSO in water to give appropriate test concentrations. Assays were carried out in 96-well filter bottom plates. Cells expressing the appropriate human transporter protein (75,000 cells/assay well) were pre-incubated at 25° C. in standard assay buffer containing either test compound, a standard inhibitor (positive control) or compound vehicle (DMSO in water; final DMSO concentration was 0.1% in each assay well) for 5 minutes. Reactions were started by addition of either $^3$H-serotonin, $^3$H-noradrenaline or $^3$H-dopamine substrates. All reactions were carried out at at 25° C. in a shaking incubator. Incubation times were 5 minutes for the hSERT and hDAT assays and 15 minutes for the hNET assay. Reactions were terminated by addition of ice-cold wash buffer (see below), followed by filtration of the assay mixture using a vacuum manifold and rapid washing with icecold wash buffer. The quantity of $^3$H-substrate incorporated into the cells was then quantified: Filtered/washed assay plates were dried at 45° C. for 1 hour, scintillation fluid added, and radioactivity measured by scintillation counting. Potency of test compounds was quantified as $IC_{50}$ values (concentration of test compound required to inhibit the specific uptake of radiolabelled substrate into the cells by 50% relative to maximum (compound vehicle only) and minimum (complete inhibition by standard inhibitor) responses).

(iii) Standard Assay Buffer Composition:

Tris(hydroxymethyl)amino methane hydrochloride (26 mM)
NaCl (124 mM)
KCl (4.5 mM)
$KH_2PO_4$ (1.2 mM)
$MgCl_2.6H_2O$ (1.3 mM)
Ascorbic acid (1.136 mM)
Glucose (5.55 mM)
pH 7.40
$CaCl_2$ (2.8 mM)
Pargyline (100 μM)
Note: The pH of the buffer was adjusted to 7.40 with 1 M NaOH before addition of $CaCl_2$ and pargyline.

Wash Buffer Composition:
Tris(hydroxymethyl)methylamine (26 mM)
NaCl (124 mM)
KCl (4.5 mM)
$KH_2PO_4$ (1.2 mM)
$MgCl_2.6H_2O$ (1.3 mM)
Ascorbic acid (1.136 mM)
pH 7.40 at 4° C. with 6M HCl (iv) Summary of Assay Parameters

|  | hSERT Assay | hDAT Assay | hNET Assay |
|---|---|---|---|
| Cells per assay well. | 75,000 | 75,000 | 75,000 |
| Substrate Concentration. | $^3$H-5HT (50 nM) | $^3$H-Dopamine (200 nM) | $^3$H-Noradrenaline (200 nM) |
| Incubation time (minutes) | 5 | 5 | 15 |

TABLE 1

| Compound | SRI $IC_{50}$ (nM) | NRI $IC_{50}$ (nM) |
|---|---|---|
| Example 1 | 13.9 | 14.1 |
| Example 2 | 9.7 | 28.5 |
| Example 3 | 22.3 | 21.2 |
| Example 4 | 18.8 | 45.9 |
| Example 5 | 10.9 | 32.9 |
| Example 6 | 45.2 | 56.9 |
| Example 7 | 5.7 | 55.4 |
| Example 8 | 7.5 | 16.7 |
| Example 9 | 5.7 | 14.0 |
| Example 10 | 7.6 | 7.7 |
| Example 11 | 3.2 | 17.0 |
| Example 12 | 21.5 | 26.3 |
| Example 13 | 8.8 | 3.1 |
| Example 14 | 43.0 | 57.1 |
| Example 15 | 17.5 | 71.6 |

Conveniently, compounds of the invention are isolated following work-up in the form of the free base, but pharmaceutically acceptable acid addition salts of the compounds of the invention may be prepared using conventional means. Solvates (e.g. hydrates) of a compound of the invention may be formed during the work-up procedure of one of the aforementioned process steps.

Where compounds were prepared in the manner described for an earlier Example, the skilled person will appreciate that it may nevertheless be necessary or desirable to employ different work-up or purification conditions.

The invention claimed is:
1. A compound of Formula (I)

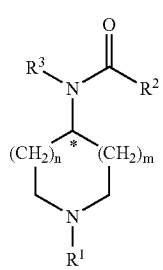

and the pharmaceutically and/or veterinarily acceptable salts thereof, wherein $R^1$ is H;
$R^2$ is phenyl, naphthyl or quinolinyl, each optionally substituted by at least one substituent independently selected from $C_{1-8}$alkyl, $C_{1-8}$alkoxy, OH, halo, $CF_3$, $OCF_3$, $SCF_3$, hydroxy-$C_{1-6}$alkyl, $C_{1-4}$alkoxy-$C_{1-6}$alkyl and $C_{1-4}$alkyl-S—$C_{1-4}$alkyl;
$R^3$ is $C_{1-6}$alkyl, $C_{3-8}$cycloalkyl, $C_{3-8}$cycloalkyl-$C_{1-6}$alkyl, aryl, het, aryl-$C_{1-4}$alkyl or het-$C_{1-4}$alkyl, wherein the cycloalkyl, aryl or het groups are optionally substituted by at least one substituent independently selected from $C_{1-6}$alkyl, $C_{1-6}$alkoxy, OH, halo, $CF_3$, $OCF_3$, $SCF_3$, hydroxy-$C_{1-6}$alkyl, $C_{1-4}$alkoxy-$C_{1-6}$alkyl and $C_{1-4}$alkyl-S—$C_{1-4}$alkyl;

n is 1, and m is 0, wherein * represents a chiral centre;

aryl is phenyl, naphthyl, anthracyl or phenanthryl; and het is an aromatic or non-aromatic 4-, 5- or 6-membered heterocycle which contains at least one N, O or S heteroatom, optionally fused to a 5- or 6-membered carbocyclic group or a second 4-, 5- or 6-membered heterocycle which contains at least one N, O or S heteroatom.

2. A compound of claim 1, wherein * represents the R or S enantiomer.

3. A compound of claim 2, wherein * represents the S enantiomer.

4. A compound of claim 1, wherein $R^2$ is phenyl or naphthyl each optionally substituted by one, two or three substituents independently selected from halo, OH, $C_{1-4}$alkyl and $CF_3$.

5. A compound of claim 1, wherein $R^3$ is $C_{1-6}$alkyl, $C_{3-8}$cycloalkyl, $C_{3-8}$cycloalkyl-$C_{1-4}$alkyl or aryl-$C_{1-4}$alkyl.

6. A compound of claim 5, wherein $R^3$ is $C_{1-6}$alkyl, $C_{3-6}$cycloalkyl, $C_{3-6}$cycloalkyl-$C_{1-2}$alkyl, phenyl-$CH_2$— or naphthyl-$CH_2$—.

7. A compound of claim 1, wherein:
$R^2$ is phenyl or naphthyl each optionally substituted by one, two or three substituents independently selected from halo, OH, $C_{1-4}$alkyl and $CF_3$; and
$R_3$ is $C_{1-6}$alkyl, $C_{3-6}$cycloalkyl, $C_{3-6}$cycloalkyl-$C_{1-3}$alkyl, phenyl-$CH_2$— or naphthyl-$CH_2$—.

8. The compound:
2,3-dichloro-N-isobutyl-N-[(3S)-pyrrolidin-3-yl]benzamide;
2,4-dichloro-N-isobutyl-N-[(3S)-pyrrolidin-3-yl]benzamide;
2-chloro-3-methyl-N-isobutyl-N-[(3S)-pyrrolidin-3-yl]benzamide;
3-fluoro-2-methyl-N-isobutyl-N-[(3S)-pyrrolidin-3-yl]benzamide;
3-methoxy-2-methyl-N-isobutyl-N-[(3S)-pyrrolidin-3-yl]benzamide;
3-chloro-N-isobutyl-N-[(3S)-pyrrolidin-3-yl]benzamide;
4-chloro-N-isobutyl-N-[(3S)-pyrrolidin-3-yl]benzamide;
3,4-dichloro-N-isobutyl-N-[(3S)-pyrrolidin-3-yl]benzamide;
N-(2-naphthylmethyl)-N-[(3S)-pyrrolidin-3-yl]benzamide;
N-(2-naphthylmethyl)-N-[(3R)-pyrrolidin-3-yl]benzamide;
N-isobutyl-N-[(3S)-pyrrolidin-3-yl]-2-naphthamide;
N-butyl-N-[(3S)-pyrrolidin-3-yl]-1-naphthamide;
4-chloro-N-(3,4-dichlorobenzyl)-N-[(3R)-pyrrolidin-3-yl]benzamide;
N-pyrrolidin-3-yl-N-(5,6,7,8-tetrahydro-naphthalen-1-ylmethyl)-benzamide;
N-(2,4-dichloro-benzyl)-N-pyrrolidin-3-yl-benzamide;
N-(3-chloro-4-methyl-benzyl)-2-fluoro-N-pyrrolidin-3-yl-benzamide;
naphthalene-2-carboxylic acid butyl-pyrrolidin-3-yl-amide;
naphthalene-2-carboxylic acid isobutyl-pyrrolidin-3-yl-amide;
naphthalene-2-carboxylic acid (2,2-dimethyl-propyl)-pyrrolidin-3-yl-amide;
3-chloro-N-isobutyl-4-methyl-N-pyrrolidin-3-yl-benzamide;
N-isobutyl-2,3-dimethyl-N-pyrrolidin-3-yl-benzamide;
3-chloro-N-(2,2-dimethyl-propyl)-2-methyl-N-pyrrolidin-3-yl-benzamide;
2-chloro-4-fluoro-N-isobutyl-N-pyrrolidin-3-yl-benzamide;
2-chloro-N-isobutyl-N-pyrrolidin-3-yl-benzamide;
3-chloro-2-fluoro-N-isobutyl-N-pyrrolidin-3-yl-benzamide;
3-chloro-4-fluoro-N-isobutyl-N-pyrrolidin-3-yl-benzamide;
N-butyl-2,4-dichloro-N-pyrrolidin-3-yl-benzamide;
2,4-dichloro-N-cyclobutylmethyl-N-pyrrolidin-3-yl-benzamide;
2,4-dichloro-N-cyclopentylmethyl-N-pyrrolidin-3-yl-benzamide;
2,4-dichloro-N-(2,2-dimethyl-propyl)-2-methyl-N-pyrrolidin-3-yl-benzamide;
2,4-dichloro-N-(2-ethyl-butyl)-N-pyrrolidin-3-yl-benzamide;
2,4-dichloro-N-(3-methyl-butyl)-N-pyrrolidin-3-yl-benzamide;
2,3,4-trichloro-N-isobutyl-N-pyrrolidin-3-yl-benzamide;
2,4-dichloro-N-(2-cyclopropyl-ethyl)-N-pyrrolidin-3-yl-benzamide;
naphthalene-1-carboxylic acid isobutyl-pyrrolidin-3-yl-amide;
2,4-dichloro-5-fluoro-N-isobutyl-N-pyrrolidin-3-yl-benzamide;
2,3-dichloro-N-(2,2-dimethyl-propyl)-N-pyrrolidin-3-yl-benzamide;
2,3-dichloro-N-(3-methyl-butyl)-N-pyrrolidin-3-yl-benzamide;
2,3-dichloro-N-cyclobutylmethyl-N-pyrrolidin-3-yl-benzamide;
2,3-dichloro-N-cyclopentyl-N-pyrrolidin-3-yl-benzamide;
3,4-dichloro-N-cyclopentyl-N-pyrrolidin-3-yl-benzamide;
2,3-dichloro-N-(1,2-dimethyl-propyl)-N-pyrrolidin-3-yl-benzamide;
2,4-dichloro-N-(1,2-dimethyl-propyl)-N-pyrrolidin-3-yl-benzamide;
2,3-dichloro-N-cyclohexyl-N-pyrrolidin-3-yl-benzamide;
2,4-dichloro-N-cyclopentyl-N-pyrrolidin-3-yl-benzamide;
3,4-dichloro-N-cyclopentyl-N-pyrrolidin-3-yl-benzamide;
naphthalene-1-carboxylic acid sec-butyl-pyrrolidin-3-yl-amide;
N-sec-butyl-2,3-dichloro-N-pyrrolidin-3-yl-benzamide;
N-sec-butyl-2,4-dichloro-N-pyrrolidin-3-yl-benzamide;
2,3-dichloro-N-(1-ethyl-propyl)-N-pyrrolidin-3-yl-benzamide;
2,4-dichloro-N-(1-ethyl-propyl)-N-pyrrolidin-3-yl-benzamide;
naphthalene-1-carboxylic acid (1-ethyl-propyl)-pyrrolidin-3-yl-amide;
2,3-dichloro-N-cyclobutyl-N-pyrrolidin-3-yl-benzamide;
2,4-dichloro-N-cyclobutyl-N-pyrrolidin-3-yl-benzamide;
2,4-dichloro-N-cyclopentyl-N-pyrrolidin-3-yl-benzamide;
2,3-dichloro-N-pyrrolidin-3-yl-N-(1,2,2-trimethyl-propyl)-benzamide;
N-tert-butyl-2,3-dichloro-N-pyrrolidin-3-yl-benzamide;

naphthalene-1-carboxylic acid cyclopentyl-pyrrolidin-3-yl-amide;
2,3-dichloro-N-phenyl-N-pyrrolidin-3-yl-benzamide;
3,4-dichloro-N-(2,2-dimethyl-propyl)-2-methyl-N-pyrrolidin-3-yl-benzamide;
3-chloro-N-isobutyl-2-methyl-N-pyrrolidin-3-yl-benzamide;
N-butyl-2,3-dichloro-N-pyrrolidin-3-yl-benzamide;
N-butyl-3,4-dichloro-N-pyrrolidin-3-yl-benzamide;
naphthalene-2-carboxylic acid cyclobutylmethyl-pyrrolidin-3-yl-amide;
naphthalene-1-carboxylic acid cyclobutylmethyl-pyrrolidin-3-yl-amide;
3,4-dichloro-N-cyclobutylmethyl-N-pyrrolidin-3-yl-benzamide;
4-chloro-N-isobutyl-2-methoxy-N-pyrrolidin-3-yl-benzamide;
4-chloro-N-isobutyl-3-methyl-N-pyrrolidin-3-yl-benzamide;
2,4-dichloro-N-isobutyl-3-methyl-N-pyrrolidin-3-yl-benzamide;
naphthalene-1-carboxylic acid (3-methyl-butyl)-pyrrolidin-3-yl-amide;
naphthalene-1-carboxylic acid (2,2-dimethyl-propyl)-pyrrolidin-3-yl-amide;
3,4-dichloro-N-(3-methyl-butyl)-N-pyrrolidin-3-yl-benzamide;
2,3-dichloro-N-(4-fluoro-phenyl)-N-pyrrolidin-3-yl-benzamide;
2,4-dichloro-N-(4-fluoro-phenyl)-N-pyrrolidin-3-yl-benzamide;
naphthalene-1-carboxylic acid (4-fluoro-phenyl)-pyrrolidin-3-yl-amide;
N-butyl-2,3,4-trichloro-N-pyrrolidin-3-yl-benzamide;
2,3,4-trichloro-N-cyclobutylmethyl-N-pyrrolidin-3-yl-benzamide;
N-pyrrolidin-3-yl-N-(3-trifluoromethyl-benzyl)-benzamide;
2,4-dichloro-N-phenyl-N-pyrrolidin-3-yl-benzamide;
3,4-dichloro-N-phenyl-N-pyrrolidin-3-yl-benzamide;
2,3,4-trichloro-N-(2,2-dimethyl-propyl)-N-pyrrolidin-3-yl-benzamide;
naphthalene-1-carboxylic acid phenyl-pyrrolidin-3-yl-amide;
2,3,4-trichloro-N-(2-cyclopropyl-ethyl)-N-pyrrolidin-3-yl-benzamide;
2,3-dichloro-N-(2-cyclopropyl-ethyl)-N-pyrrolidin-3-yl-benzamide;
2-bromo-4-chloro-N-isobutyl-N-pyrrolidin-3-yl-benzamide;
4-chloro-2-ethoxy-N-isobutyl-N-pyrrolidin-3-yl-benzamide;
3-bromo-4-chloro-N-isobutyl-N-pyrrolidin-3-yl-benzamide;
2,4-dichloro-5-fluoro-N-isobutyl-N-[(3S)-pyrrolidin-3-yl]benzamide;
3,4-dichloro-N-isobutyl-2-methyl-N-pyrrolidin-3-yl-benzamide;
2,4-dichloro-3-fluoro-N-isobutyl-N-[pyrrolidin-3-yl]benzamide;
2,3-dichloro-4-fluoro-N-isobutyl-N-[pyrrolidin-3-yl]benzamide;
2,3-dichloro-5-fluoro-N-isobutyl-N-[pyrrolidin-3-yl]benzamide;
2,4,5-trichloro-N-isobutyl-N-[pyrrolidin-3-yl]benzamide;
2,5-dichloro-N-isobutyl-N-[pyrrolidin-3-yl]benzamide;
2,5-dichloro-4-fluoro-N-isobutyl-N-[pyrrolidin-3-yl]benzamide;
2,3,5-trichloro-N-isobutyl-N-[pyrrolidin-3-yl]benzamide;
2,3-dichloro-6-fluoro-N-isobutyl-N-[pyrrolidin-3-yl]benzamide;
3,4-dichloro-6-fluoro-N-isobutyl-N-[pyrrolidin-3-yl]benzamide;
3,4-dichloro-2-fluoro-N-isobutyl-N-[pyrrolidin-3-yl]benzamide;
2-chloro-3,6-difluoro-N-isobutyl-N-[pyrrolidin-3-yl]benzamide; and
4-chloro-N-(2,3-dichlorobenzyl)-N-[(3R)-pyrrolidin-3-yl]benzamide, or pharmaceutically and/or veterinarily acceptable salts thereof.

9. The compound 2,3-dichloro-N-isobutyl-N-[(3S)-pyrrolidin-3-yl]benzamide, or pharmaceutically and/or veterinarily acceptable salts thereof.

10. The compound 2,3-dichloro-N-cyclopentyl-N-pyrrolidin-3-yl-benzamide, or pharmaceutically and/or veterinarily acceptable salts thereof.

11. A pharmaceutical composition comprising a therapeutically effective amount of a compound of claim 1, and a pharmaceutically acceptable adjuvant, diluent or carrier.

12. A method of treating urinary incontinence, which comprises administering a therapeutically effective amount of a compound of claim 1 to a patient in need of such treatment.

13. A process for preparing a compound of claim 1 comprising reacting a compound of formula (X):

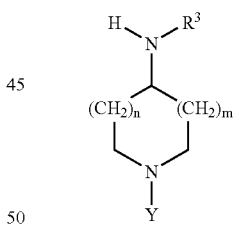

wherein $R^3$, n and m are as defined above and Y is $R^1$ or a protecting group, with an acid or acyl halide: $R^2COX$, wherein X is OH or halo, and deprotecting if necessary or desired.

* * * * *